US009259023B2

(12) United States Patent
Oestergaard et al.

(10) Patent No.: US 9,259,023 B2
(45) Date of Patent: Feb. 16, 2016

(54) PROCESS FOR MAKING A MILK-BASED PROTEIN HYDROLYSATE

(75) Inventors: Peter Rahbek Oestergaard, Virum (DK); Steffen Ernst, Broenshoej (DK); Gitte B. Lynglev, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 416 days.

(21) Appl. No.: 12/752,207

(22) Filed: Apr. 1, 2010

(65) Prior Publication Data

US 2010/0255153 A1 Oct. 7, 2010

Related U.S. Application Data

(60) Provisional application No. 61/166,295, filed on Apr. 3, 2009.

(30) Foreign Application Priority Data

Apr. 2, 2009 (EP) .................................... 09157185

(51) Int. Cl.
| | |
|---|---|
| A23J 3/34 | (2006.01) |
| A23J 1/20 | (2006.01) |
| A23L 1/305 | (2006.01) |
| A23L 1/29 | (2006.01) |
| C12N 9/52 | (2006.01) |
| C12N 9/58 | (2006.01) |
| C12N 9/64 | (2006.01) |
| C12N 9/76 | (2006.01) |

(52) U.S. Cl.
CPC ............... *A23L 1/296* (2013.01); *A23L 1/3053* (2013.01); *A23L 1/3056* (2013.01); *C12N 9/52* (2013.01); *C12N 9/58* (2013.01); *C12N 9/6424* (2013.01); *C12N 9/6427* (2013.01)

(58) Field of Classification Search
CPC ..... A23L 1/296; A23L 1/3053; A23L 1/3056; C12N 9/6427; C12N 9/58; C12N 9/6424; C12N 9/52
See application file for complete search history.

(56) References Cited

U.S. PATENT DOCUMENTS

| | | | |
|---|---|---|---|
| 4,918,008 | A | 4/1990 | Gauri |
| 4,981,704 | A | 1/1991 | Thibault |
| 5,039,532 | A | 8/1991 | Jost et al. |
| 6,036,983 | A | 3/2000 | Nielsen |
| 8,153,396 | B2 * | 4/2012 | Lynglev et al. ............. 435/68.1 |
| 8,222,372 | B2 * | 7/2012 | Budolfsen et al. ............ 530/350 |
| 2001/0026797 | A1 * | 10/2001 | Sjoeholm et al. ............ 424/94.6 |
| 2005/0037368 | A1 | 2/2005 | Klotz et al. |
| 2005/0089969 | A1 | 4/2005 | Wissler et al. |
| 2006/0147499 | A1 | 7/2006 | Oestergaard et al. |
| 2008/0096794 | A1 | 4/2008 | Boehm et al. |

FOREIGN PATENT DOCUMENTS

| | | |
|---|---|---|
| EP | 0 631 731 | 1/1995 |
| JP | 4 248959 | 4/1992 |
| JP | 6 343422 | 12/1994 |
| JP | 2005-350452 | 12/2005 |
| JP | 2007091669 | 4/2007 |
| WO | WO 87/01286 | 3/1987 |
| WO | WO 92/21248 | 12/1992 |
| WO | WO 93/04593 | 3/1993 |
| WO | WO 93/24020 | 12/1993 |
| WO | 99/65326 A1 | 12/1999 |
| WO | WO 00/15655 | 3/2000 |
| WO | WO 01/70047 | 9/2001 |
| WO | WO 02/00852 | 1/2002 |
| WO | WO 03/059083 | 7/2003 |
| WO | WO 2004/047566 | 6/2004 |
| WO | 2004/072221 A2 | 8/2004 |
| WO | 2004/111220 A1 | 12/2004 |
| WO | WO 2006/061631 | 6/2006 |
| WO | 2008/131008 A2 | 10/2008 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut-ons in Each Repeat, J. Mol. BIoL (2002) 324, 373-386.*
Machine translated JP 06343422, enclosed, pp. 1-5. Translated 2012.*
Translated JP 04248959, enclosed, pp. 1-28. Translated 2012.*
Rival et al, Journal Agricultural Food Chem. vol. 49, pp. 287-294 (2001).
Plavsic et al, Biopharma Intl, pp. 1-2 (2001).
Rypniewski et al, Acta Crystallographica Section D, Biological Cystallography, vol. D57, pp. 8-19 (2001).
Screen et al, The Journal of Biological Chemistry, vol. 275, No. 9, pp. 6689-6694 (2000).
English-language document that is a Japanese to English translation of Japanese Patent Application Publication No. JP 04248959 (including track changes from the translation of Japanese Patent Application Publication No. JP 04248959, translated on Sep. 2012.

* cited by examiner

*Primary Examiner* — Julie Ha
*Assistant Examiner* — Li Ni Komatsu
(74) *Attorney, Agent, or Firm* — Kristin McNamara

(57) ABSTRACT

The present invention relates to an enzymatic process for making a milk-based protein hydrolysate and use of such hydrolysate, e.g., in an infant formula composition.

8 Claims, 2 Drawing Sheets

SEQUENCE LISTING

<160> NUMBER OF SEQ ID NOS: 19

<210> SEQ ID NO 1
<211> LENGTH: 744
<212> TYPE: DNA
<213> ORGANISM: Fusarium oxysporum

<400> SEQUENCE: 1

```
atggtcaagt tcgcttccgt cgttgcactt gttgctcccc tggctgctgc cgctcctcag      60
gagatcccca acattgttgg tggcacttct gccagcgctg gcgactttcc cttcatcgtg     120
agcattagcc gcaacggtgg cccctggtgt ggaggttctc tcctcaacgc caacaccgtc     180
ttgactgctg cccactgcgt ttccggatac gctcagagcg gtttccagat tcgtgctggc     240
agtctgtctc gcacttctgg tggtattacc tcctcgcttt cctccgtcag agttcaccct     300
agctacagcg gaaacaacaa cgatcttgct attctgaagc tctctacttc catcccctcc     360
ggcggaaaca tcggctatgc tcgcctggct gcttccggct ctgaccctgt cgctggatct     420
tctgccactg ttgctggctg gggcgctacc tctgagggcg gcagctctac tcccgtcaac     480
cttctgaagg ttactgtccc tatcgtctct cgtgctacct gccgagctca gtacggcacc     540
tccgccatca ccaaccagat gttctgtgct ggtgtttctt ccggtggcaa ggactcttgc     600
cagggtgaca gcggcggccc catcgtcgac agctccaaca ctcttatcgg tgctgtctct     660
tggggtaacg gatgtgcccg acccaactac tctggtgtct atgccagcgt tggtgctctc     720
cgctctttca ttgacaccta tgct                                            744
```

<210> SEQ ID NO 2
<211> LENGTH: 248
<212> TYPE: PRT
<213> ORGANISM: Fusarium oxysporum

```
<400> SEQUENCE: 2

Met Val Lys Phe Ala Ser Val Val Ala Leu Val Ala Pro Leu Ala Ala
1               5                   10                  15

Ala Ala Pro Gln Glu Ile Pro Asn Ile Val Gly Gly Thr Ser Ala Ser
            20                  25                  30

Ala Gly Asp Phe Pro Phe Ile Val Ser Ile Ser Arg Asn Gly Gly Pro
        35                  40                  45

Trp Cys Gly Gly Ser Leu Leu Asn Ala Asn Thr Val Leu Thr Ala Ala
    50                  55                  60

His Cys Val Ser Gly Tyr Ala Gln Ser Gly Phe Gln Ile Arg Ala Gly
65                  70                  75                  80

Ser Leu Ser Arg Thr Ser Gly Ile Thr Ser Ser Leu Ser Ser Val
                85                  90                  95

Arg Val His Pro Ser Tyr Ser Gly Asn Asn Asn Asp Leu Ala Ile Leu
                100                 105                 110

Lys Leu Ser Thr Ser Ile Pro Ser Gly Gly Asn Ile Gly Tyr Ala Arg
            115                 120                 125

Leu Ala Ala Ser Gly Ser Asp Pro Val Ala Gly Ser Ser Ala Thr Val
    130                 135                 140

Ala Gly Trp Gly Ala Thr Ser Glu Gly Gly Ser Ser Thr Pro Val Asn
145                 150                 155                 160

Leu Leu Lys Val Thr Val Pro Ile Val Ser Arg Ala Thr Cys Arg Ala
                165                 170                 175

Gln Tyr Gly Thr Ser Ala Ile Thr Asn Gln Met Phe Cys Ala Gly Val
            180                 185                 190

Ser Ser Gly Gly Lys Asp Ser Cys Gln Gly Asp Ser Gly Gly Pro Ile
        195                 200                 205

Val Asp Ser Ser Asn Thr Leu Ile Gly Ala Val Ser Trp Gly Asn Gly
    210                 215                 220

Cys Ala Arg Pro Asn Tyr Ser Gly Val Tyr Ala Ser Val Gly Ala Leu
225                 230                 235                 240

Arg Ser Phe Ile Asp Thr Tyr Ala
                245

<210> SEQ ID NO 3
<211> LENGTH: 753
<212> TYPE: DNA
<213> ORGANISM: Fusarium solani

<400> SEQUENCE: 3
atggtcaagt tgctgccat cctcgcactt gttgcgcctc ttgtcgccgc tcggcctcag       60
gactcatcac ccatgatcgt tggtggaact gctgccagcg ctggtgactt ccccttcatc    120
gtcagcatcg cctacaatgg tggcccttgg tgcggaggta ccctcctcaa cgccaacacc    180
gtcatgactg ctgcccactg cacccaaggt cgctctgcta cgccttcca ggtccgcgcc     240 ggaagtctga accgcaactc gggtggtgtt acctcttccg tttcttccat caggatccat    300
cctagcttca gtagctcgac cctgaacaac gatgtttcca tcctgaagct gtccaccccc    360
atctcgacta gctccactat ttcttatggt cgcctggctg cgtcgggctc tgaccctgtt    420
gccggctctg atgccacagt tgctggctgg ggtgtcactt ctcagggctc ttccagctct    480
cccgtggctt tgaggaaggt taccattccc atcgtctccc gcaccactt ccgatcccag     540 tatggcactt ctgccatcac caccaacatg ttctgcgctg gtcttgctga gggtggtaag    600
gactcttgcc agggcgacag cggcggtccc attgtcgata cctccaacac tgtcattggc    660
```

```
attgtttctt ggggtgaggg ttgtgctcag cccaacttat ctggtgtcta tgcccgagtt    720
ggatctctcc gcacttacat cgacggccag ctg                                 753
```

<210> SEQ ID NO 4
<211> LENGTH: 251
<212> TYPE: PRT
<213> ORGANISM: Fusarium solani

<400> SEQUENCE: 4

```
Met Val Lys Phe Ala Ala Ile Leu Ala Leu Val Ala Pro Leu Val Ala
1               5                   10                  15

Ala Arg Pro Gln Asp Ser Ser Pro Met Ile Val Gly Gly Thr Ala Ala
            20                  25                  30

Ser Ala Gly Asp Phe Pro Phe Ile Val Ser Ile Ala Tyr Asn Gly Gly
        35                  40                  45

Pro Trp Cys Gly Gly Thr Leu Leu Asn Ala Asn Thr Val Met Thr Ala
    50                  55                  60

Ala His Cys Thr Gln Gly Arg Ser Ala Ser Ala Phe Gln Val Arg Ala
65                  70                  75                  80

Gly Ser Leu Asn Arg Asn Ser Gly Gly Val Thr Ser Val Ser Ser
                85                  90                  95

Ile Arg Ile His Pro Ser Phe Ser Ser Ser Thr Leu Asn Asn Asp Val
            100                 105                 110

Ser Ile Leu Lys Leu Ser Thr Pro Ile Ser Ser Ser Thr Ile Ser
        115                 120                 125

Tyr Gly Arg Leu Ala Ala Ser Gly Ser Asp Pro Val Ala Gly Ser Asp
    130                 135                 140

Ala Thr Val Ala Gly Trp Gly Val Thr Ser Gln Gly Ser Ser Ser Ser
145                 150                 155                 160

Pro Val Ala Leu Arg Lys Val Thr Ile Pro Ile Val Ser Arg Thr Thr
                165                 170                 175

Cys Arg Ser Gln Tyr Gly Thr Ser Ala Ile Thr Thr Asn Met Phe Cys
            180                 185                 190

Ala Gly Leu Ala Glu Gly Gly Lys Asp Ser Cys Gln Gly Asp Ser Gly
        195                 200                 205

Gly Pro Ile Val Asp Thr Ser Asn Thr Val Ile Gly Ile Val Ser Trp
    210                 215                 220

Gly Glu Gly Cys Ala Gln Pro Asn Leu Ser Gly Val Tyr Ala Arg Val
225                 230                 235                 240

Gly Ser Leu Arg Thr Tyr Ile Asp Gly Gln Leu
                245                 250
```

<210> SEQ ID NO 5
<211> LENGTH: 750
<212> TYPE: DNA
<213> ORGANISM: Fusarium cf. solani

<400> SEQUENCE: 5

```
atggtcaagt tgctgccat cctcgcactt gttgcgcctc ttgtcgccgc tcggcctcag     60
gaccgaccca tgattgtcgg cggaactgct gccagcgcag gtgacttccc cttcatcgtc    120
agcatcgcct acaatggtgg cccttggtgc ggaggtaccc tcctcaacgc cagcaccgtc    180
ttgactgctg cccactgcac ccaaggtcgc tctgctagcg ccttccaggt ccgcgctgga    240
agcttgaacc gcaactcggg tggtgttacc tctgccgttt cttccatccg gatccatcct    300
```

```
agcttcagtg gctcgaccct gaacaacgat gtttctatcc tgaagctgtc cacccccatc        360
tcgactagct ccaccatctc ttatggtcgc ttggctgcgt cgggctccga ccctgctgcc        420
ggctctgatg ccacagttgc tggctggggt gtcacttctc agggctcttc cagctccccc        480
gtcgctttga ggaaggttac cattcccatt gtctctcgca ccacttgccg atcccagtat        540
ggcacttctg ccatcaccac caacatgttc tgcgctggcc ttgctgaggg tggaaaggac        600
tcttgccagg cgacagcgg tggtcccatt gtcgacacct ccaacactgt cattggcatt         660
gtttcttggg gtgagggttg tgctcagccc aacttctctg gtgtctatgc ccgcgttggc        720
agcctccgct cttacattga cggccagctg                                          750
```

<210> SEQ ID NO 6
<211> LENGTH: 250
<212> TYPE: PRT
<213> ORGANISM: Fusarium cf. solani

<400> SEQUENCE: 6

```
Met Val Lys Phe Ala Ala Ile Leu Ala Leu Val Ala Pro Leu Val Ala
1               5                   10                  15

Ala Arg Pro Gln Asp Arg Pro Met Ile Val Gly Gly Thr Ala Ala Ser
            20                  25                  30

Ala Gly Asp Phe Pro Phe Ile Val Ser Ile Ala Tyr Asn Gly Gly Pro
        35                  40                  45

Trp Cys Gly Gly Thr Leu Leu Asn Ala Ser Thr Val Leu Thr Ala Ala
    50                  55                  60

His Cys Thr Gln Gly Arg Ser Ala Ser Ala Phe Gln Val Arg Ala Gly
65                  70                  75                  80

Ser Leu Asn Arg Asn Ser Gly Gly Val Thr Ser Ala Val Ser Ser Ile
                85                  90                  95

Arg Ile His Pro Ser Phe Ser Gly Ser Thr Leu Asn Asn Asp Val Ser
            100                 105                 110

Ile Leu Lys Leu Ser Thr Pro Ile Ser Thr Ser Thr Ile Ser Tyr
        115                 120                 125

Gly Arg Leu Ala Ala Ser Gly Ser Asp Pro Ala Gly Ser Asp Ala
    130                 135                 140

Thr Val Ala Gly Trp Gly Val Thr Ser Gln Gly Ser Ser Ser Pro
145                 150                 155                 160

Val Ala Leu Arg Lys Val Thr Ile Pro Ile Val Ser Arg Thr Thr Cys
                165                 170                 175

Arg Ser Gln Tyr Gly Thr Ser Ala Ile Thr Thr Asn Met Phe Cys Ala
            180                 185                 190

Gly Leu Ala Glu Gly Gly Lys Asp Ser Cys Gln Gly Asp Ser Gly Gly
        195                 200                 205

Pro Ile Val Asp Thr Ser Asn Thr Val Ile Gly Ile Val Ser Trp Gly
    210                 215                 220

Glu Gly Cys Ala Gln Pro Asn Phe Ser Gly Val Tyr Ala Arg Val Gly
225                 230                 235                 240

Ser Leu Arg Ser Tyr Ile Asp Gly Gln Leu
                245                 250
```

<210> SEQ ID NO 7
<211> LENGTH: 1596
<212> TYPE: DNA
<213> ORGANISM: Nocardiopsis sp. NRRL 18262

<400> SEQUENCE: 7

```
acgtttggta cgggtaccgg tgtccgcatg tggccagaat gccccttgc gacagggaac      60
ggattcggtc ggtagcgcat cgactccgac aaccgcgagg tggccgttcg cgtcgccacg    120
ttctgcgacc gtcatgcgac ccatcatcgg gtgaccccac cgagctctga atggtccacc    180
gttctgacgg tctttccctc accaaaacgt gcacctatgg ttaggacgtt gtttaccgaa    240
tgtctcggtg aacgacaggg gccggacggt attcggcccc gatccccgt tgatccccc     300
aggagagtag ggaccccatg cgaccctccc ccgttgtctc cgccatcggt acgggagcgc    360
tggccttcgg tctggcgctg tccggtaccc cgggtgccct cgcggccacc ggagcgctcc    420
cccagtcacc caccccggag gccgacgcgg tctccatgca ggaggcgctc cagcgcgacc    480
tcgacctgac ctccgccgag gccgaggagc tgctggccgc ccaggacacc gccttcgagg    540
tcgacgaggc cgcggccgag gccgccgggg acgcctacgg cggctccgtc ttcgacaccg    600
agagcctgga actgaccgtc ctggtcaccg atgccgccgc ggtcgaggcc gtggaggcca    660
ccggcgccgg gaccgagctg gtctcctacg gcatcgacgg tctcgacgag atcgtccagg    720
agctcaacgc cgccgacgcc gttcccggtg tggtcggctg gtacccggac gtggcgggtg    780
acaccgtcgt cctggaggtc ctggagggtt ccggagccga cgtcagcggc ctgctcgcgg    840
acgccggcgt ggacgcctcg gccgtcgagg tgaccacgag cgaccagccc gagctctacg    900
ccgacatcat cggtggtctg gcctacacca tgggcgccg ctgttcggtc ggcttcgcgg    960
ccaccaacgc cgccggtcag cccgggttcg tcaccgccgg tcactgcggc cgcgtgggca   1020
cccaggtgac catcggcaac ggcaggggcg tcttcgagca gtccgtcttc cccggcaacg   1080
acgcggcctt cgtccgcggt acgtccaact tcacgctgac caacctggtc agccgctaca   1140
acaccggcgg gtacgccacg gtcgccggtc acaaccaggc ccccatcggc tcctccgtct   1200
gccgctccgg ctccaccacc ggttggcact gcggcaccat ccaggcccgc ggccagtcgg   1260
tgagctaccc cgagggcacc gtcaccaaca tgacccggac caccgtgtgc gccgagcccg   1320
gcgactccgg cggctcctac atctccggca cccaggccca gggcgtgacc tccggcggct   1380
ccggcaactg ccgcaccggc gggaccacct tctaccagga ggtcacccc atggtgaact   1440
cctggggcgt ccgtctccgg acctgatccc cgcggttcca ggcggaccga cggtcgtgac   1500
ctgagtacca ggcgtccccg ccgcttccag cggcgtccgc accggggtgg gaccgggcgt   1560
ggccacggcc ccacccgtga ccggaccgcc cggcta                             1596
```

<210> SEQ ID NO 8
<211> LENGTH: 188
<212> TYPE: PRT
<213> ORGANISM: Nocardiopsis sp. NRRL 18262

<400> SEQUENCE: 8

```
Ala Asp Ile Ile Gly Gly Leu Ala Tyr Thr Met Gly Gly Arg Cys Ser
1               5                  10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
```

```
                   85                   90                   95
Gly Ser Ser Val Cys Arg Ser Gly Thr Thr Gly Trp His Cys Gly
                100                  105                  110

Thr Ile Gln Ala Arg Gly Gln Ser Val Ser Tyr Pro Glu Gly Thr Val
            115                  120                  125

Thr Asn Met Thr Arg Thr Thr Val Cys Ala Glu Pro Gly Asp Ser Gly
        130                  135                  140

Gly Ser Tyr Ile Ser Gly Thr Gln Ala Gln Gly Val Thr Ser Gly Gly
    145                  150                  155                  160

Ser Gly Asn Cys Arg Thr Gly Gly Thr Thr Phe Tyr Gln Glu Val Thr
                165                  170                  175

Pro Met Val Asn Ser Trp Gly Val Arg Leu Arg Thr
            180                  185
```

<210> SEQ ID NO 9
<211> LENGTH: 1125
<212> TYPE: DNA
<213> ORGANISM: Metarhizium anisopliae

<400> SEQUENCE: 9

```
atggagctta ccaaatttct tgccttactg gcagttatcc tgcccgtcgc ctacggtgca      60
ccaacgcagg cggcaagcct gcaccccag attttggagg ccatgaagcg cgacttgggg     120
ctgaacgccg agcaggccac tgttcgtgtg gcgcgggaga tccatgccac cgatgttatt    180
gagcagctgc gcagctcagt agcgttcgct ggtgcttgga ttgacgcgga cgtgctatac    240
atcggcatta ctgaccaagc cttggccgat gaggtcactg ctgccggcgc cacgccgatt    300
gtcatgacca acagcctgtc caagctggaa aaggccaagg aggatctcga taagatattc    360
atcggccgag ccaacaccct ggaaacatct tcggacacta gctctggcat tgcatcgtat    420
ttcgttgatg tcgccgccaa caagctcgtt atagaggctc tcgccgacag tcacggccat    480
gctgagcaac tagccgcgca ggtttgggct tacatccgaat tcgaggtgcg gactgttgag    540
acgatgccga ctaccatggc cacggttcag ggtggtgatg tctattatat taatagaagc    600
tcccgctgct ctatcggttt cgcagtaacc acaggtttcg tgtccgctgg acactgtgga    660
ggatcaggag cttcagctac aacaagtagt ggtgaggccc taggaacctt tcgggctcc    720
gtcttccctg cagtgccga catggcctac gtccgcactg taagtggaac agtccttaga    780
ggctacatca acggctacgg ccaagggagc tttcccgtct caggaagctc cgaggctgcc    840
gttggagcta gcatctgccg ctccggctca accactcaag tccactgcgg cacgattggt    900
gccaagggcg ccacggttaa ctaccctcaa ggagctgttt cgggcctcac tcggactagc    960
gtctgcgccg agcccggcga ctcaggcggt tctttctact ccggctccca ggcgcagggt    1020
gtcacctcgg gaggcagcgg cgactgcagc cgtggaggca cgacctattt ccagcctgtt    1080
aataggatcc tccagacata tggccttacc ttggtcacgg cgtag                    1125
```

<210> SEQ ID NO 10
<211> LENGTH: 374
<212> TYPE: PRT
<213> ORGANISM: Metarhizium anisopliae

<400> SEQUENCE: 10

```
Met Glu Leu Thr Lys Phe Leu Ala Leu Leu Ala Val Ile Leu Pro Val
1               5                   10                  15

Ala Tyr Gly Ala Pro Thr Gln Ala Ala Ser Leu His Pro Gln Ile Leu
            20                  25                  30
```

Glu Ala Met Lys Arg Asp Leu Gly Leu Asn Ala Glu Gln Ala Thr Val
                35                  40                  45

Arg Val Ala Arg Glu Ile His Ala Thr Asp Val Ile Glu Gln Leu Arg
 50                  55                  60

Ser Ser Val Ala Phe Ala Gly Ala Trp Ile Asp Ala Asp Val Leu Tyr
 65                  70                  75                  80

Ile Gly Ile Thr Asp Gln Ala Leu Ala Asp Glu Val Thr Ala Ala Gly
                85                  90                  95

Ala Thr Pro Ile Val Met Thr Asn Ser Leu Ser Lys Leu Glu Lys Ala
                100                 105                 110

Lys Glu Asp Leu Asp Lys Ile Phe Ile Gly Arg Ala Asn Thr Leu Glu
                115                 120                 125

Thr Ser Ser Asp Thr Ser Ser Gly Ile Ala Ser Tyr Phe Val Asp Val
130                 135                 140

Ala Ala Asn Lys Leu Val Ile Glu Ala Leu Ala Asp Ser His Gly His
145                 150                 155                 160

Ala Glu Gln Leu Ala Ala Gln Val Gly Leu Thr Ser Glu Phe Glu Val
                165                 170                 175

Arg Thr Val Glu Thr Met Pro Thr Thr Met Ala Thr Val Gln Gly Gly
                180                 185                 190

Asp Val Tyr Tyr Ile Asn Arg Ser Ser Arg Cys Ser Ile Gly Phe Ala
                195                 200                 205

Val Thr Thr Gly Phe Val Ser Ala Gly His Cys Gly Gly Ser Gly Ala
                210                 215                 220

Ser Ala Thr Thr Ser Ser Gly Glu Ala Leu Gly Thr Phe Ser Gly Ser
225                 230                 235                 240

Val Phe Pro Gly Ser Ala Asp Met Ala Tyr Val Arg Thr Val Ser Gly
                245                 250                 255

Thr Val Leu Arg Gly Tyr Ile Asn Gly Tyr Gly Gln Gly Ser Phe Pro
                260                 265                 270

Val Ser Gly Ser Ser Glu Ala Ala Val Gly Ala Ser Ile Cys Arg Ser
                275                 280                 285

Gly Ser Thr Thr Gln Val His Cys Gly Thr Ile Gly Ala Lys Gly Ala
                290                 295                 300

Thr Val Asn Tyr Pro Gln Gly Ala Val Ser Gly Leu Thr Arg Thr Ser
305                 310                 315                 320

Val Cys Ala Glu Pro Gly Asp Ser Gly Ser Phe Tyr Ser Gly Ser
                325                 330                 335

Gln Ala Gln Gly Val Thr Ser Gly Gly Ser Gly Asp Cys Ser Arg Gly
                340                 345                 350

Gly Thr Thr Tyr Phe Gln Pro Val Asn Arg Ile Leu Gln Thr Tyr Gly
                355                 360                 365

Leu Thr Leu Val Thr Ala
    370

<210> SEQ ID NO 11
<211> LENGTH: 1400
<212> TYPE: DNA
<213> ORGANISM: Brachysporiella gayana

<400> SEQUENCE: 11
gtaggagctg tagaatcagc acatgaggca agtataaaag aaccagcatg ggatgatcaa    60
agtctgccaa ttcaaaggag caccatcaag ccgtcttgtc tagaactcct tgaacaccct   120

-continued

```
gtctactcca gtactcttgt cacagaacac atctagatat ggagctcaca agcctcatcg    180
ccgcactcgc agttattctg cctattgcct acggtgttcc catggatgcc accaccaacc    240
tttctcccaa ggtcctggcc gctatgaagc gcgacctggg acttgacgcc agggaggcca    300
ctgcccgtgt caccttcgaa cgtcgtgctg gcgatgtcat cgaggagctg cgcagctccc    360
tgggagattc gttcgccggt gcttgggtta cggatggcaa ggtcatcaac attggtgtca    420
ctgatcaagc tttggtctcc aaggttaagg aagctggcgc tgaaccgatg gttatgaaga    480
acagcctcgg gaagcttcaa gaggcaaaga agaagcttga tcagatcatc aaggagaagc    540
cgaagaccct cagcacctca ggcaagcccg gcattgcaac atactacgtt gacattgaga    600
ccaacaagct catcatcacg gcactctcca ccagtatcac tcaagctgaa gatctggcta    660
aggaggttgg cctttctgag tctgagttcg aggtgcgcaa gactgagaag atgccatccc    720 cttcatcct cggcggagac ccctttgtca tcaacaacag tgccgtgtgc tctgtcggct    780
tcgccgtctc tggcgggttt gtctcagctg gccactgtgg cggtcaaggc agccctgtca    840
cctatatcga cggtggcgca cttggaacga tcgaaggatc tgtcttcccc ggtgatgcag    900
atatgtcctt catccgtgcc gttgacggca ctgacctccc tggcatcgtt ggtacctatg    960
gcaacggtga tcagcccatc tttggcagca atgtcgcacc catcggctct ggtgtctgcc   1020
gctcaggaac aactaccggc tatcactgcg gccagcttga tgcctacgac gtcactgtca   1080
actacgacgt gggacctgtg ttcggtctta ccatgacctc tgcttgcgct gagcctggag   1140
actctggcgg ctccttcttt gccggtgacc aggctcaggg cgtcacctcg ggaggttctg   1200
gtgattgcac cagcggtggt cagaccttct tccagcccgt gaacgagatt ctggagacct   1260
atggtctctc gctcaccacg gcctaattgg atgaggcttt ggacagccaa gagcctcaac   1320
ttttcatctg tatatagcaa ttattttcgt atctcaagta cttagatcgt cacgatcaat   1380
acatatggac ttcgcttggc                                               1400
```

<210> SEQ ID NO 12
<211> LENGTH: 375
<212> TYPE: PRT
<213> ORGANISM: Brachysporiella gayana

<400> SEQUENCE: 12

```
Met Glu Leu Thr Ser Leu Ile Ala Ala Leu Ala Val Ile Leu Pro Ile
1               5                   10                  15

Ala Tyr Gly Val Pro Met Asp Ala Thr Thr Asn Leu Ser Pro Lys Val
            20                  25                  30

Leu Ala Ala Met Lys Arg Asp Leu Gly Leu Asp Ala Arg Glu Ala Thr
        35                  40                  45

Ala Arg Val Thr Phe Glu Arg Arg Ala Gly Asp Val Ile Glu Glu Leu
    50                  55                  60

Arg Ser Ser Leu Gly Asp Ser Phe Ala Gly Ala Trp Val Thr Asp Gly
65                  70                  75                  80

Lys Val Ile Asn Ile Gly Val Thr Asp Gln Ala Leu Val Ser Lys Val
                85                  90                  95

Lys Glu Ala Gly Ala Glu Pro Met Val Met Lys Asn Ser Leu Gly Lys
            100                 105                 110

Leu Gln Glu Ala Lys Lys Leu Asp Gln Ile Ile Lys Glu Lys Pro
        115                 120                 125

Lys Thr Leu Ser Thr Ser Gly Lys Pro Gly Ile Ala Thr Tyr Tyr Val
    130                 135                 140
```

```
Asp Ile Glu Thr Asn Lys Leu Ile Ile Thr Ala Leu Ser Thr Ser Ile
145                 150                 155                 160

Thr Gln Ala Glu Asp Leu Ala Lys Glu Val Gly Leu Ser Glu Ser Glu
                165                 170                 175

Phe Glu Val Arg Lys Thr Glu Lys Met Pro Ser Pro Phe Ile Leu Gly
            180                 185                 190

Gly Asp Pro Phe Val Ile Asn Asn Ser Ala Val Cys Ser Val Gly Phe
        195                 200                 205

Ala Val Ser Gly Gly Phe Ser Ala Gly His Cys Gly Gly Gln Gly
    210                 215                 220

Ser Pro Val Thr Tyr Ile Asp Gly Gly Ala Leu Gly Thr Ile Glu Gly
225                 230                 235                 240

Ser Val Phe Pro Gly Asp Ala Asp Met Ser Phe Ile Arg Ala Val Asp
            245                 250                 255

Gly Thr Asp Leu Pro Gly Ile Val Gly Thr Tyr Gly Asn Gly Asp Gln
        260                 265                 270

Pro Ile Phe Gly Ser Asn Val Ala Pro Ile Gly Ser Gly Val Cys Arg
    275                 280                 285

Ser Gly Thr Thr Thr Gly Tyr His Cys Gly Gln Leu Asp Ala Tyr Asp
290                 295                 300

Val Thr Val Asn Tyr Asp Val Gly Pro Val Phe Gly Leu Thr Met Thr
305                 310                 315                 320

Ser Ala Cys Ala Glu Pro Gly Asp Ser Gly Gly Ser Phe Phe Ala Gly
            325                 330                 335

Asp Gln Ala Gln Gly Val Thr Ser Gly Gly Ser Gly Asp Cys Thr Ser
        340                 345                 350

Gly Gly Gln Thr Phe Phe Gln Pro Val Asn Glu Ile Leu Glu Thr Tyr
    355                 360                 365

Gly Leu Ser Leu Thr Thr Ala
370                 375

<210> SEQ ID NO 13
<211> LENGTH: 162
<212> TYPE: PRT
<213> ORGANISM: Bos taurus

<400> SEQUENCE: 13

Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
            20                  25                  30

Asp Ala Gln Ser Ala Pro Leu Arg Val Tyr Val Glu Glu Leu Lys Pro
        35                  40                  45

Thr Pro Glu Gly Asp Leu Glu Ile Leu Leu Gln Lys Trp Glu Asn Gly
    50                  55                  60

Glu Cys Ala Gln Lys Lys Ile Ile Ala Glu Lys Thr Lys Ile Pro Ala
65                  70                  75                  80

Val Phe Lys Ile Asp Ala Leu Asn Glu Asn Lys Val Leu Val Leu Asp
            85                  90                  95

Thr Asp Tyr Lys Lys Tyr Leu Leu Phe Cys Met Glu Asn Ser Ala Glu
        100                 105                 110

Pro Glu Gln Ser Leu Ala Cys Gln Cys Leu Val Arg Thr Pro Glu Val
    115                 120                 125

Asp Asp Glu Ala Leu Glu Lys Phe Asp Lys Ala Leu Lys Ala Leu Pro
130                 135                 140
```

```
Met His Ile Arg Leu Ser Phe Asn Pro Thr Gln Leu Glu Glu Gln Cys
145                 150                 155                 160

His Ile

<210> SEQ ID NO 14
<211> LENGTH: 11
<212> TYPE: PRT
<213> ORGANISM: Artificial Sequence
<220> FEATURE:
<223> OTHER INFORMATION: Fragment - aa 91-101 of Bos taurus
      betalactoglobulin

<400> SEQUENCE: 14

Lys Val Leu Val Leu Asp Thr Asp Tyr Lys Lys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Fragment - aa 30-41 of Bos taurus
      betalactoglobulin

<400> SEQUENCE: 15

Ser Leu Leu Asp Ala Gln Ser Ala Pro Leu Arg Val
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Fragment - aa 24-41 of Bos taurus
      betalactoglobulin

<400> SEQUENCE: 16

Met Ala Ala Ser Asp Ile Ser Leu Leu Asp Ala Gln Ser Ala Pro Leu
1               5                   10                  15

Arg Val

<210> SEQ ID NO 17
<211> LENGTH: 22
<212> TYPE: PRT
<213> ORGANISM: Artificial Sequence
<220> FEATURE:
<223> OTHER INFORMATION: Fragment - aa 40-61 of Bos taurus
      betalactoglobulin

<400> SEQUENCE: 17

Arg Val Tyr Val Glu Glu Leu Lys Pro Thr Pro Glu Gly Asp Leu Glu
1               5                   10                  15

Ile Leu Leu Gln Lys Trp
            20

<210> SEQ ID NO 18
<211> LENGTH: 16
<212> TYPE: PRT
<213> ORGANISM: Artificial Sequence
<220> FEATURE:
<223> OTHER INFORMATION: Fragment - aa 122-137 of Bos taurus
      betalactoglobulin

<400> SEQUENCE: 18

Leu Val Arg Thr Pro Glu Val Asp Asp Glu Ala Leu Glu Lys Phe Asp
```

-continued

```
1               5               10              15

<210> SEQ ID NO 19
<211> LENGTH: 17
<212> TYPE: PRT
<213> ORGANISM: Artificial Sequence
<220> FEATURE:
<223> OTHER INFORMATION: Fragment - aa 42-58 of Bos taurus
      betalactoglobulin

<400> SEQUENCE: 19

Tyr Val Glu Glu Leu Lys Pro Thr Pro Glu Gly Asp Leu Glu Ile Leu
1               5                   10                  15

Leu
```

PROCESS FOR MAKING A MILK-BASED PROTEIN HYDROLYSATE

CROSS-REFERENCE TO RELATED APPLICATIONS

This application claims priority or the benefit under 35 U.S.C. 119 of European application no. 09157185.1 filed Apr. 2, 2009 and U.S. provisional application No. 61/166,295 filed Apr. 3, 2009, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to an enzymatic process for making a milk-based protein hydrolysate and use of such hydrolysate, e.g., in an infant formula composition.

BACKGROUND OF THE INVENTION

Infant formulae have been developed, which allow for substituting breast feeding of infants.

Such infant formulae should wholly satisfy the nutritional requirements of infants until the introduction of appropriate complementary feeding. Further, taste is important, as at least the parents prefer infant formulae having a non-bitter taste. Infant formulae which instead of ordinary cow's milk comprise hydrolyzed milk protein, e.g. partially hydrolyzed whey protein or extensively hydrolyzed casein, are often used as such formulae are less allergenic and still have an acceptable taste.

Processes for preparation of partial hydrolysates described in the literature often comprise use of pancreatic enzymes such as trypsin preparations produced by extraction of porcine pancreatic tissue (see, e.g., WO9304593 A1, U.S. Pat. No. 5,039,532 A). Some of the processes described comprise use of a mixture of trypsin and chymotrypsin. E.g., EP0353122 A discloses a process for preparing a hypoallergenic whey protein hydrolysate using a mixture of trypsin and chymotrypsin, wherein the ratio of the chymotrypsin/trypsin activities is between 1.5 and 3.0. In EP0631731 A1, a mixture of trypsin and chymotrypsin having a trypsin to chymotrypsin ratio of 1.3 to 18 in USP units, more preferably 4 to 6, is said to typically result in a hydrolysate of desirable properties.

For several reasons, use of proteolytic enzymes produced from a microorganism may confer benefits. For example, enzyme production from a microorganism is efficient and easy to control. Therefore, such enzymes can be produced in large quantities and at high purity. Also, use of microbial enzymes will help overcoming increasing QA related difficulties as regards extraction of enzymes from an animal source.

One object for the present inventors has been to develop a process for making a milk-based protein hydrolysate with microbially produced enzymes which has a low allergenicity. Another object has been to develop a process for making a milk-based protein hydrolysate with microbially produced enzymes which has a protein fragment profile having similarity to the protein fragment profile of hydrolysates prepared with extracted preparations comprising trypsin and chymotrypsin. Another object has been to develop a process for making a milk-based protein hydrolysate with microbially produced enzymes which has an acceptable taste. In particular, it would be highly desirable to have a partial whey protein hydrolysate which has low allergenicity, which has a protein fragment profile having similarity to the protein fragment profile of hydrolysates prepared with extracted preparations comprising trypsin and chymotrypsin, and/or which has an acceptable taste, in particular as regards bitterness.

SUMMARY OF THE INVENTION

The present inventors have surprisingly found that microbially produced enzymes can be used for production of a milk-based protein hydrolysate, e.g., for inclusion into an infant formula.

The invention therefore relates to a process for the preparation of a milk-based protein hydrolysate comprising treatment of a solution of a milk-based proteinaceous material with a) a trypsin-like endopeptidase produced from a microorganism, and b) at least one other endopeptidase produced from a microorganism.

DETAILED DESCRIPTION OF THE INVENTION

Figure 1:
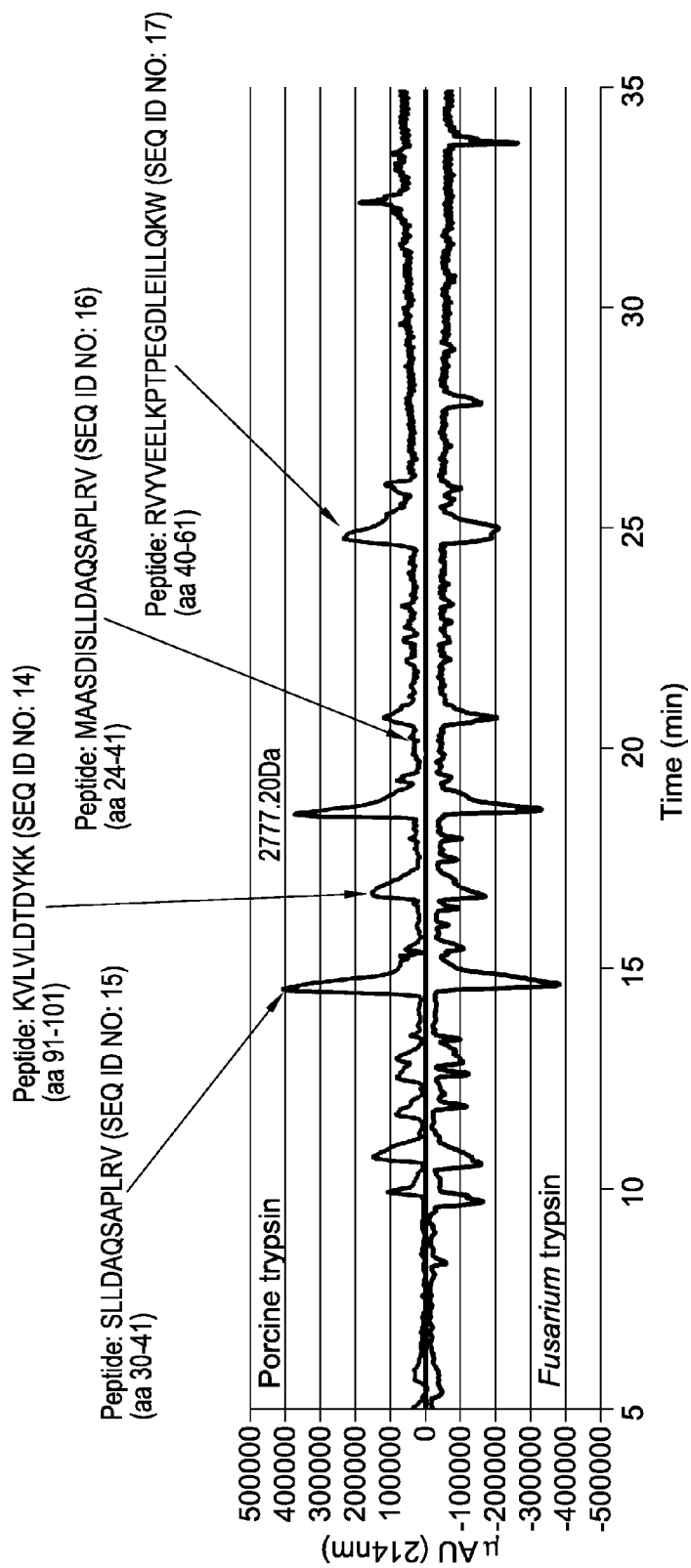
FIG. 1 shows UV-chromatograms of *Fusarium* trypsin (bottom trace) compared with porcine trypsin (upper trace) and the peptide sequence identity of some major peaks are displayed.

In the process according to the invention, a milk-based proteinaceous material is used as starting material. Such milk-based proteinaceous material may, e.g., consist of whey-based proteinaceous material, casein or mixtures of whey-based proteinaceous material and casein. The whey-based proteinaceous material may be sourced from a whey obtained from cheese making, particularly a sweet whey such as that resulting from the coagulation of casein by rennet. The whey-based proteinaceous material may also be used in the form of concentrates in the range of 35-80% protein as obtained by ultrafiltration (UF whey), or from whey protein isolates. This whey-based proteinaceous material, optionally, may also be demineralized by ion exchange and/or electrodialysis (ED whey). In a preferred embodiment, the milk-based proteinaceous material is whey protein concentrate (WPC).

The casein source may be acid casein or non-fat milk solids.

The whey-based proteinaceous material and/or the casein may be used, e.g., in the form of liquid concentrates or powders.

In a preferred embodiment, the milk-based proteinaceous material is a whey-based proteinaceous material. In a more preferred embodiment, the source of such whey-based proteinaceous material is sweet whey from which the caseino-glyco-macropeptide (CGMP) has been removed or whey protein isolate. In an even more preferred embodiment, the source of such whey-based proteinaceous material is sweet whey from which the caseino-glyco-macropeptide has been removed.

Removal of the CGMP from sweet whey results in a protein material with a threonine content closer to that of human milk. This modified sweet whey can then be supplemented with those amino acids in respect of which it has a low content (principally histidine and arginine). A process for removing CGMP from sweet whey is described in EP 880902.

For the process of the invention, the proteinaceous material is diluted or reconstituted to solutions or suspensions, preferably comprising around 2-35% by weight of proteinaceous material, more preferably around 5-30% by weight.

In the process of the invention, the milk-based proteinaceous material is treated with at least two endopeptidases, which have both been produced from a microorganism.

Such endopeptidases to be used in the process of the invention may be produced from a microorganism of any genus. For purposes of the present invention, the term "produced from" as used herein in connection with a given organism shall mean that the polypeptide used according to the invention is produced by fermentation of a cell of the given organism. The polypeptide may be native to the organism from which it is produced or it may be produced heterologously from a host organism in which a nucleotide sequence encoding the polypeptide has been inserted.

One of the endopeptidases to be used in a process according to the invention is a trypsin-like endopeptidase. The term "trypsin-like endopeptidase" is defined herein as an endopeptidase which preferentially cleaves peptides or proteins at the C-terminal side of the L-isomer of arginine and/or lysine.

In a preferred embodiment, the trypsin-like endopeptidase preferentially cleaves peptides or proteins at the C-terminal side of arginine and lysine. This means that the endopeptidase has a higher specificity for cleaving after both of arginine and lysine than it has for cleaving after any other amino acid.

In another preferred embodiment, the trypsin-like endopeptidase preferentially cleaves peptides or proteins at the C-terminal side of arginine or lysine. This means that the endopeptidase has a higher specificity for cleaving after any of arginine or lysine than it has for cleaving after any other amino acid.

In another preferred embodiment, the trypsin-like endopeptidase preferentially cleaves peptides or proteins at the C-terminal side of arginine. This means that the endopeptidase has a higher specificity for cleaving after arginine than it has for cleaving after any other amino acid.

In another preferred embodiment, the trypsin-like endopeptidase preferentially cleaves peptides or proteins at the C-terminal side of lysine. This means that the endopeptidase has a higher specificity for cleaving after lysine than it has for cleaving after any other amino acid.

In another preferred embodiment, the trypsin-like endopeptidase specifically cleaves peptides or proteins at the C-terminal side of arginine and lysine.

A trypsin-like endopeptidase according to the invention in a preferred embodiment has a Trypsin ratio of more than 100, wherein the Trypsin ratio is determined as the activity of the enzyme when cleaving after Arg or Lys (whichever is the larger) divided by the activity of the enzyme when cleaving after any one of Ala, Asp, Glu, Ile, Leu, Met, Phe or Val (whichever is the larger). I.e., in a preferred embodiment, a trypsin-like endopeptidase according to the invention has a specificity for cleaving after Arg or Lys (whichever is the larger) which is at least 100-fold higher than its specificity for cleaving after any one of Ala, Asp, Glu, Ile, Leu, Met, Phe or Val (whichever is the larger). Such activity measurements to determine the Trypsin ratio should be performed at a pH-value where the activity of the endopeptidase is at least half of the activity of the endopeptidase at its pH optimum. The Trypsin ratio may be determined as described in Example 1 of the present application.

Typically, such trypsin-like endopeptidase has optimal proteolytic activity at a pH from about 6.0 to about 11.0, preferably at a pH from about 8 to about 10, and at a temperature from about 40° C. to about 70° C., preferably at a temperature from about 45° C. to about 65° C. or from about 45° C. to about 60° C.

In a preferred embodiment, the trypsin-like endopeptidase is a fungal endopeptidase. In a more preferred embodiment, the trypsin-like endopeptidase is derived from a strain of *Fusarium*, preferably *Fusarium oxysporum*. It may, e.g., have the amino acid sequence of the mature polypeptide of SEQ ID NO: 2 of the present application (SWISSPROT No. P35049). A trypsin-like endopeptidase from *Fusarium oxysporum* having the amino acid sequence shown as amino acids 25-248 of SEQ ID NO: 2 has previously been described (U.S. Pat. No. 5,288,627; U.S. Pat. No. 5,693,520).

In one embodiment, the trypsin-like endopeptidase is derived from *Fusarium solani*, e.g. AP977S having the amino acid sequence shown as SEQ ID NO: 4 of the present application (GENESEQP: ADZ80577). In another embodiment, the trypsin-like endopeptidase is derived from *Fusarium* cf. *solani*, e.g. AP971 having the amino acid sequence shown as SEQ ID NO: 6 of the present application.

For purposes of the present invention, the term "derived from" as used herein in connection with deriving a polynucleotide or a polypeptide from a given source (i.e., a biological organism) may mean that the polynucleotide (or the polynucleotide encoding the polypeptide) is identical to or a variant of a polynucleotide sequence naturally present in that source organism, irrespective if the polynucleotide sequence has been inserted into or the polypeptide is produced by another organism.

In a preferred embodiment, the trypsin-like endopeptidase is produced from a fungus. In a more preferred embodiment, the trypsin-like endopeptidase is produced from a strain of *Fusarium*.

In a preferred embodiment of the invention, the trypsin-like endopeptidase is selected from the group consisting of:
i) a polypeptide comprising an amino acid sequence having at least 60% identity to the mature polypeptide of any of SEQ ID NOs: 2, 4 or 6;
ii) a polypeptide encoded by a polynucleotide that hybridizes under at least low stringency conditions with (i) the mature polypeptide coding sequence of any of SEQ ID NOs: 1, 3 or 5, (ii) the genomic DNA sequence comprising the mature polypeptide coding sequence of any of SEQ ID NOs: 1, 3 or 5, or (iii) a full-length complementary strand of (i) or (ii);
iii) a polypeptide encoded by a polynucleotide comprising a nucleotide sequence having at least 60% identity to the mature polypeptide coding sequence of any of SEQ ID NOs: 1, 3 or 5; and
iv) a variant comprising a substitution, deletion, and/or insertion of one or more (several) amino acids of the mature polypeptide of any of SEQ ID NOs: 2, 4 or 6.

The term "mature polypeptide" is defined herein as a polypeptide having endopeptidase activity that is in its final form following translation and any post-translational modifications, such as N-terminal processing, C-terminal truncation, glycosylation, phosphorylation, etc.

The term "mature polypeptide coding sequence" is defined herein as a nucleotide sequence that encodes a mature polypeptide having endopeptidase activity.

The mature polypeptide of SEQ ID NO: 2 may be amino acids 25-248. The mature polypeptide of SEQ ID NO: 4 may be amino acids 26-251. The mature polypeptide of SEQ ID NO: 6 may be amino acids 18-250.

For purposes of the present invention, the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

In one preferred embodiment of the invention, the trypsin-like endopeptidase comprises an amino acid sequence having at least 60%, preferably at least 70% or at least 80%, more preferably at least 85% or at least 90%, even more preferably at least 95%, and most preferably at least 98% identity to the mature polypeptide of SEQ ID NO: 2. In a more preferred embodiment of the invention, the trypsin-like endopeptidase comprises the amino acid sequence of the mature polypeptide of SEQ ID NO: 2. In another more preferred embodiment of the invention, the trypsin-like endopeptidase comprises amino acids 25 to 248 of SEQ ID NO: 2. In an even more preferred embodiment of the invention, the trypsin-like endopeptidase consists of the amino acid sequence of the mature polypeptide of SEQ ID NO: 2. In another even more preferred embodiment of the invention, the trypsin-like endopeptidase consists of amino acids 25 to 248 of SEQ ID NO: 2.

In another preferred embodiment of the invention, the trypsin-like endopeptidase comprises an amino acid sequence having at least 60%, preferably at least 70% or at least 80%, more preferably at least 85% or at least 90%, even more preferably at least 95%, and most preferably at least 98% identity to the mature polypeptide of SEQ ID NO: 4. In a more preferred embodiment of the invention, the trypsin-like endopeptidase comprises the amino acid sequence of the mature polypeptide of SEQ ID NO: 4. In another more preferred embodiment of the invention, the trypsin-like endopeptidase comprises amino acids 26 to 251 of SEQ ID NO: 4. In an even more preferred embodiment of the invention, the trypsin-like endopeptidase consists of the amino acid sequence of the mature polypeptide of SEQ ID NO: 4. In another even more preferred embodiment of the invention, the trypsin-like endopeptidase consists of amino acids 26 to 251 of SEQ ID NO: 4.

In another preferred embodiment of the invention, the trypsin-like endopeptidase comprises an amino acid sequence having at least 60%, preferably at least 70% or at least 80%, more preferably at least 85% or at least 90%, even more preferably at least 95%, and most preferably at least 98% identity to the mature polypeptide of SEQ ID NO: 6. In a more preferred embodiment of the invention, the trypsin-like endopeptidase comprises the amino acid sequence of the mature polypeptide of SEQ ID NO: 6. In another more preferred embodiment of the invention, the trypsin-like endopeptidase comprises amino acids 18 to 250 of SEQ ID NO: 6. In an even more preferred embodiment of the invention, the trypsin-like endopeptidase consists of the amino acid sequence of the mature polypeptide of SEQ ID NO: 6. In another even more preferred embodiment of the invention, the trypsin-like endopeptidase consists of amino acids 18 to 250 of SEQ ID NO: 6.

In another preferred embodiment of the invention, the trypsin-like endopeptidase is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions, with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii). (J. Sambrook, E. F. Fritsch, and T. Maniatis, 1989, Molecular Cloning, A Laboratory Manual, 2d edition, Cold Spring Harbor, N.Y.).

In another preferred embodiment of the invention, the trypsin-like endopeptidase is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions, with (i) the mature polypeptide coding sequence of SEQ ID NO: 3, (ii) the genomic DNA sequence comprising the mature polypeptide coding sequence of SEQ ID NO: 3, or (iii) a full-length complementary strand of (i) or (ii).

In another preferred embodiment of the invention, the trypsin-like endopeptidase is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions, with (i) the mature polypeptide coding sequence of SEQ ID NO: 5, (ii) the genomic DNA sequence comprising the mature polypeptide coding sequence of SEQ ID NO: 5, or (iii) a full-length complementary strand of (i) or (ii).

In the context of the present invention, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

In another preferred embodiment of the invention, the trypsin-like endopeptidase is encoded by a polynucleotide comprising a nucleotide sequence having at least 60%, preferably at least 70% or at least 80%, more preferably at least 85% or at least 90%, even more preferably at least 95%, and most preferably at least 98%, identity to the mature polypeptide coding sequence of SEQ ID NO: 1.

In another preferred embodiment of the invention, the trypsin-like endopeptidase is encoded by a polynucleotide comprising a nucleotide sequence having at least 60%, preferably at least 70% or at least 80%, more preferably at least 85% or at least 90%, even more preferably at least 95%, and most preferably at least 98%, identity to the mature polypeptide coding sequence of SEQ ID NO: 3.

In another preferred embodiment of the invention, the trypsin-like endopeptidase is encoded by a polynucleotide comprising a nucleotide sequence having at least 60%, preferably at least 70% or at least 80%, more preferably at least 85% or at least 90%, even more preferably at least 95%, and most preferably at least 98%, identity to the mature polypeptide coding sequence of SEQ ID NO: 5.

In another preferred embodiment of the invention, the trypsin-like endopeptidase is a variant comprising a substitution, deletion, and/or insertion of one or more (several) amino acids of the mature polypeptide of any of SEQ ID NOs: 2, 4 or 6.

In the context of the present invention, such variant may be an allelic (natural) variant or it may be an artificial variant. It may comprise a substitution, deletion, and/or insertion of one or more (or several) amino acids of a mature polypeptide. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an anti-genic epitope or a binding domain.

The concentration of trypsin-like endopeptidase is preferably 1,000-1,000,000 USP Trypsin Units per g milk-based protein, more preferably 5,000-500,000, and most preferably 25,000-250,000.

One USP Trypsin Unit is the activity causing a change in absorbance at 253 nm of 0.003 at pH 7.6 and 25° C. using N-benzoyl-L-arginine ethyl ester hydrochloride (BAEE) as substrate.

The specific activity may vary quite significantly among different trypsin-like endopeptidases, but the skilled person will easily be able to determine in which amount the trypsin-like endopeptidase is to be used, e.g. based on the degree of hydrolysis.

The ratio of trypsin-like endopeptidase to milk-based protein is preferably 0.01-10% weight/weight, more preferably 0.01-5%, more preferably 0.05-2.5%, even more preferably 0.5-1%, and most preferably around 0.75%.

In a process according to the present invention, a milk-based proteinaceous material is treated with a trypsin-like endopeptidase and at least one other endopeptidase.

In a preferred embodiment, the at least one other endopeptidase is a serine endopeptidase.

In another preferred embodiment, the at least one other endopeptidase has an activity which is less specific than the trypsin-like endopeptidase.

In another preferred embodiment, the at least one other endopeptidase has an activity which resembles the activity of mammalian chymotrypsin, e.g., chymotrypsin extracted from porcine pancreatic tissue.

In another preferred embodiment, the at least one other endopeptidase has a higher specificity for cleaving at the carboxy-terminal side of either of tyrosine, phenylalanine, tryptophan, leucine, methionine or histidine than for cleaving on the carboxy-terminal side of any other natural amino acid.

In another preferred embodiment, the at least one other endopeptidase has a specificity for cleaving at the carboxy-terminal side of at least one of tyrosine, phenylalanine, tryptophan, leucine, methionine or histidine, which is at least 3-fold higher, preferably at least 5-fold higher, than its specificity for cleaving at the carboxy-terminal side of either one of alanine, arginine, asparagine, aspartic acid, cysteine, glutamic acid, glutamine, glycine, isoleucine, lysine, proline, serine, threonine and valine.

In another preferred embodiment, the at least one other endopeptidase has a higher specificity for cleaving at the carboxy-terminal side of each of at least three amino acids from the group consisting of tyrosine, phenylalanine, tryptophan, leucine, methionine and histidine than for cleaving on the carboxy-terminal side of arginine.

In another preferred embodiment, the at least one other endopeptidase has a higher specificity for cleaving at the carboxy-terminal side of each of at least three amino acids from the group consisting of tyrosine, phenylalanine, tryptophan, leucine, methionine and histidine than for cleaving on the carboxy-terminal side of lysine.

In another preferred embodiment, the at least one other endopeptidase has a higher specificity for cleaving at the carboxy-terminal side of each of tyrosine, phenylalanine, tryptophan, leucine, methionine and histidine than for cleaving on the carboxy-terminal side of both of arginine and lysine.

In another preferred embodiment, the at least one other endopeptidase has a Chymotrypsin ratio of at least 3, preferably at least 5. A Chymotrypsin ratio of at least 5 means that the activity of the enzyme when cleaving after one of Phe, Leu or Met (whichever is the larger) is at least five times higher than the activity when cleaving after any one of Ala, Arg, Asp, Glu, Ile, Lys or Val (whichever is the larger). I.e., the at least one other endopeptidase has a specificity for cleaving after one of Phe, Leu or Met (whichever is the larger) which is at least 3-fold higher, preferably at least 5-fold higher, than its specificity for cleaving after any one of Ala, Arg, Asp, Glu, Ile, Lys or Val (whichever is the larger). Such activity measurements to determine the Chymotrypsin ratio should be performed at a pH-value where the activity of the endopeptidase is at least half of the activity of the endopeptidase at its pH optimum. The Chymotrypsin ratio may be determined as described in Example 1 of the present application.

In another preferred embodiment, the at least one other endopeptidase is a bacterial endopeptidase. In a more preferred embodiment, the at least one other endopeptidase is derived from a strain of *Nocardiopsis*, preferably from *Nocardiopsis* sp. NRRL 18262 (previously described in, e.g., WO 88/03947). It may, e.g., have the amino acid sequence of the mature polypeptide of SEQ ID NO: 8 of the present application. The DNA and amino acid sequences of the protease derived from *Nocardiopsis* sp. NRRL 18262 have previously been published in, e.g., DK patent application no. 1996 00013.

In another more preferred embodiment, the at least one other endopeptidase is derived from *Metarhizium*, preferably *Metarhizium anisopliae*, e.g. having the amino acid sequence of the mature polypeptide of SEQ ID NO: 10 of the present application (TREMBL:Q9Y843). In another more preferred embodiment, the at least one other endopeptidase is derived from *Brachysporiella*, preferably *Brachysporiella gayana*, e.g. having the amino acid sequence of the mature polypeptide of SEQ ID NO: 12 of the present application (CGMCC 0865). The DNA and amino acid sequences of the proteases derived from *Metarhizium anisopliae* and *Brachysporiella gayana* have previously been published in, e.g., WO04072279.

In another preferred embodiment, the at least one other endopeptidase is produced from a bacterium.

In another preferred embodiment of the invention, the at least one other endopeptidase is selected from the group consisting of:
i) a polypeptide comprising an amino acid sequence having at least 60% identity to the mature polypeptide of any of SEQ ID NOs: 8, 10 or 12;
ii) a polypeptide encoded by a polynucleotide that hybridizes under at least low stringency conditions with (i) the mature polypeptide coding sequence of any of SEQ ID NOs: 7, 9 or 11, (ii) the genomic DNA sequence comprising the mature polypeptide coding sequence of any of SEQ ID NOs: 7, 9 or 11, or (iii) a full-length complementary strand of (i) or (ii);
iii) a polypeptide encoded by a polynucleotide comprising a nucleotide sequence having at least 60% identity to the mature polypeptide coding sequence of any of SEQ ID NOs: 7, 9 or 11; and
iv) a variant comprising a substitution, deletion, and/or insertion of one or more (several) amino acids of the mature polypeptide of any of SEQ ID NOs: 8, 10 or 12.

The mature polypeptide of SEQ ID NO: 10 may be amino acids 187-374. The mature polypeptide of SEQ ID NO: 12 may be amino acids 190-375.

In another preferred embodiment of the invention, the at least one other endopeptidase comprises an amino acid sequence having at least 60%, preferably at least 70% or at least 80%, more preferably at least 85% or at least 90%, even more preferably at least 95%, and most preferably at least 98% identity to the mature polypeptide of SEQ ID NO: 8. In a more preferred embodiment of the invention, the at least one other endopeptidase comprises the amino acid sequence of the mature polypeptide of SEQ ID NO: 8. In another more preferred embodiment of the invention, the at least one other endopeptidase comprises amino acids 1 to 188 of SEQ ID NO: 8. In an even more preferred embodiment of the invention, the at least one other endopeptidase consists of the amino acid sequence of the mature polypeptide of SEQ ID NO: 8. In another even more preferred embodiment of the invention, the at least one other endopeptidase consists of amino acids 1 to 188 of SEQ ID NO: 8.

In another preferred embodiment of the invention, the at least one other endopeptidase comprises an amino acid sequence having at least 60%, preferably at least 70% or at least 80%, more preferably at least 85% or at least 90%, even more preferably at least 95%, and most preferably at least 98% identity to the mature polypeptide of SEQ ID NO: 10. In a more preferred embodiment of the invention, the at least one other endopeptidase comprises the amino acid sequence of the mature polypeptide of SEQ ID NO: 10. In another more preferred embodiment of the invention, the at least one other endopeptidase comprises amino acids 187 to 374 of SEQ ID NO: 10. In an even more preferred embodiment of the invention, the at least one other endopeptidase consists of the amino acid sequence of the mature polypeptide of SEQ ID NO: 10. In another even more preferred embodiment of the invention, the at least one other endopeptidase consists of amino acids 187 to 374 of SEQ ID NO: 10.

In another preferred embodiment of the invention, the at least one other endopeptidase comprises an amino acid sequence having at least 60%, preferably at least 70% or at least 80%, more preferably at least 85% or at least 90%, even more preferably at least 95%, and most preferably at least 98% identity to the mature polypeptide of SEQ ID NO: 12. In a more preferred embodiment of the invention, the at least one other endopeptidase comprises the amino acid sequence of the mature polypeptide of SEQ ID NO: 12. In another more preferred embodiment of the invention, the at least one other endopeptidase comprises amino acids 190 to 375 of SEQ ID NO: 12. In an even more preferred embodiment of the invention, the at least one other endopeptidase consists of the amino acid sequence of the mature polypeptide of SEQ ID NO: 12. In another even more preferred embodiment of the invention, the at least one other endopeptidase consists of amino acids 190 to 375 of SEQ ID NO: 12.

In another preferred embodiment of the invention, the at least one other endopeptidase is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions, with (i) the mature polypeptide coding sequence of SEQ ID NO: 7, (ii) the genomic DNA sequence comprising the mature polypeptide coding sequence of SEQ ID NO: 7, or (iii) a full-length complementary strand of (i) or (ii).

In another preferred embodiment of the invention, the at least one other endopeptidase is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions, with (i) the mature polypeptide coding sequence of SEQ ID NO: 9, (ii) the genomic DNA sequence comprising the mature polypeptide coding sequence of SEQ ID NO: 9, or (iii) a full-length complementary strand of (i) or (ii).

In another preferred embodiment of the invention, the at least one other endopeptidase is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions, with (i) the mature polypeptide coding sequence of SEQ ID NO: 11, (ii) the genomic DNA sequence comprising the mature polypeptide coding sequence of SEQ ID NO: 11, or (iii) a full-length complementary strand of (i) or (ii).

In another preferred embodiment of the invention, the at least one other endopeptidase is encoded by a polynucleotide comprising a nucleotide sequence having at least 60%, preferably at least 70% or at least 80%, more preferably at least 85% or at least 90%, even more preferably at least 95%, and most preferably at least 98%, identity to the mature polypeptide coding sequence of SEQ ID NO: 7.

In another preferred embodiment of the invention, the at least one other endopeptidase is encoded by a polynucleotide comprising a nucleotide sequence having at least 60%, preferably at least 70% or at least 80%, more preferably at least 85% or at least 90%, even more preferably at least 95%, and most preferably at least 98%, identity to the mature polypeptide coding sequence of SEQ ID NO: 9.

In another preferred embodiment of the invention, the at least one other endopeptidase is encoded by a polynucleotide comprising a nucleotide sequence having at least 60%, preferably at least 70% or at least 80%, more preferably at least 85% or at least 90%, even more preferably at least 95%, and most preferably at least 98%, identity to the mature polypeptide coding sequence of SEQ ID NO: 11.

In another preferred embodiment of the invention, the trypsin-like endopeptidase is a variant comprising a substitution, deletion, and/or insertion of one or more (several) amino acids of the mature polypeptide of any of SEQ ID NOs: 8, 10 or 12.

The concentration of the at least one other endopeptidase is preferably 100-100,000 USP Chymotrypsin Units per g milk-based protein, more preferably 500-50,000, and most preferably 1,000-20,000.

One USP Chymotrypsin Unit is the activity causing a change in absorbance at 237 nm of 0.0075 at pH 7.0 and 25° C. using N-acetyl-L-tyrosine ethyl ester (ATEE) as substrate.

The specific activity may vary quite significantly among different endopeptidases, but the skilled person will easily be able to determine in which amount the at least one other endopeptidase is to be used, e.g. based on the degree of hydrolysis.

The ratio of the at least one other endopeptidase to milk-based protein is preferably 0.001-1% weight/weight, more preferably 0.001-0.5%, more preferably 0.005-0.25%, even more preferably 0.02-0.1%, and most preferably around 0.05%.

Preferably, the at least one other endopeptidase is added at a concentration which is between 2% and 50% of the concentration of trypsin-like endopeptidase added based on the weight of the endopeptidases, more preferably between 5% and 20%, even more preferably between 5% and 15%, and most preferably about 10%.

Preferably, the activity of the trypsin-like endopeptidase measured in USP Trypsin Units is between 5-fold and 500-fold higher, more preferably between 10-fold and 200-fold higher, than the activity of the at least one other endopeptidase measured in USP Chymotrypsin Units.

An optional preliminary step prior to hydrolysis is preheating of the solution or suspension of milk-based proteinaceous material, e.g., to ensure denaturation of whey protein fractions, e.g., serum albumin (BSA), α-lactalbumin, β-lactoglobulin and immunoglobulins (particularly IgG). This step usually results in a diminished residual antigenicity when assessed immunochemically (as described hereinafter). In a preferred embodiment, a pre-treatment step is performed which comprises heating of the proteinaceous material at about 75-95° C. for about 5-30 minutes. In another preferred embodiment, a pre-treatment step is performed which comprises heating of the proteinaceous material at above 135° C. for about 1-5 seconds. In another preferred embodiment, a pre-treatment step is performed which comprises heating of the proteinaceous material at about 130° C. for about 30-60 seconds.

The skilled person will know which conditions to preferably apply for the hydrolysis reaction. It may be carried out, e.g., as disclosed in U.S. Pat. No. 5,039,532 or EP0631731A1. It may, e.g., be conducted at a temperature of about 40° C. to 60° C., during 1 to 6 hours, at pH values within the range 6.5 to 8.5, preferably 6.5 to 8.

In a preferred embodiment, following a first treatment with the peptidases, the proteinaceous material is further subjected to a second proteolytic hydrolysis followed by endopeptidase inactivation. In a more preferred embodiment, the proteinaceous material is subjected to a heat treatment in between the first and the second proteolytic hydrolysis as disclosed in U.S. Pat. No. 5,039,532.

Irrespective of the conditions of the hydrolysis, the hydrolysate preferably is subjected to an additional step of inactivation of the endopeptidases. This peptidase inactivation in a preferred embodiment comprises a heat treatment of about 0.1 to 30 min at a temperature of about 70 to 110° C., preferably 75 to 95° C. Alternatively, the endopeptidases may be inactivated by sterilization at ultra-high temperature (e.g., at about 130° C. for about 30-60 seconds).

The protein hydrolysate obtained may be further clarified. It may be stored in a liquid state. The hydrolysate may also be ultrafiltrated, it may be concentrated, e.g., by evaporation, and it may be dried, e.g., by spray drying or lyophilization.

In a preferred embodiment, the protein hydrolysate obtained has a moderate degree of hydrolysis. In another preferred embodiment, the protein hydrolysate obtained is a partial hydrolysate. In another preferred embodiment, the protein hydrolysate obtained has a degree of hydrolysis of between 5 and 30%, preferably between 10 and 25% and more preferably between 12 and 20%. A particularly preferred degree of hydrolysis is around 14%. Another particularly preferred degree of hydrolysis is around 15%.

The degree of hydrolysis (DH) expresses the extent of the protein hydrolysis obtained by the method. In the context of the invention, the degree of hydrolysis (DH) is defined as follows:

$$DH = (\text{Number of peptide bonds cleaved/Total number of peptide bonds}) \times 100\%$$

Degree of hydrolysis (DH) of the protein hydrolysate obtained may be measured spectrophotometrically according to the method of Church, F. C. et al. (1983) Spectrophotometric Assay Using o-Phthaldialdehyde for Determination of Proteolysis in Milk and Isolated Milk Proteins, *J. Dairy Sci.* 66: 1219-1227.

The molecular weight distribution of the peptides in the protein hydrolysate obtained may be determined, e.g., by size exclusion chromatography (SEC). In a preferred embodiment, the hydrolysate of the invention is comprised of peptides where less than 1% on a weight-basis has a molecular weight of above 20,000 kDa.

The hydrolysate obtained by the method of the invention is preferably devoid of detectable intact milk protein. The absence of intact milk protein in the hydrolysate may be demonstrated by sodium dodecylsulfate-polyacrylamide gel electrophoresis (SDS-PAGE). Direct comparison between a hydrolysate and the non-hydrolyzed protein starting material can be made in the same gel. In a preferred embodiment, the hydrolysate of the invention is comprised of peptides where less than 1% on a weight-basis is intact milk-based protein.

The residual antigenicity of the hydrolysate obtained by the method of the invention may be determined using an enzyme-linked immunosorbent assay (ELISA). Non-hydrolyzed milk protein is immobilized on a solid phase at concentrations that fall within the linear dose response range established in the assay. Hydrolysate preparations are similarly immobilized. Subsequent, sequential incubations with rabbit anti-cow milk protein and an enzyme conjugate reactive with rabbit IgG reveals the presence of antigenically recognizable proteins and peptides. Results obtained with the hydrolysate are compared on a mass basis to those obtained with the non-hydrolyzed protein starting material. The percent antigenicity reduction of the hydrolysate is then calculated.

In a preferred embodiment, the protein hydrolysate obtained by a process according to the invention has a reduction in antigenicity of at least about 80%, preferably at least about 85%, more preferably at least about 90% or at least about 95%, most preferably at least about 98%, and even most preferably the reduction in antigenicity is at least about 99%, relative to the corresponding non-hydrolyzed milk-based proteinaceous material as measured by ELISA.

In a preferred embodiment, the protein hydrolysate obtained by a process according to the invention is for an infant formula composition.

In a preferred embodiment, the invention relates to a process for the preparation of an infant formula composition, which comprises the steps of obtaining a milk-based protein hydrolysate as disclosed above and which further comprises a step of including the milk-based protein hydrolysate into an infant formula composition.

Such infant formula composition may be in the form of a powder, a concentrated liquid, or a ready-to-use liquid.

Such infant formula composition preferably contains ingredients which are designed to meet the nutritional needs of a human infant. Thus, in addition to a protein hydrolysate obtained according to a process of the invention, the infant formula should preferably contain a lipid source, a carbohydrate source and other nutrients such as vitamins and minerals. Typically, animal oils, vegetable oils, starch, sucrose, lactose and/or corn syrup solids may be added to the formula to supply part or all of the above nutrients.

It is preferred that an infant formula composition comprising a protein hydrolysate of the invention is nutritionally complete. By the term "nutritionally complete" is meant that the composition contains adequate nutrients to sustain healthy human life for extended periods.

In a preferred embodiment, an infant formula composition comprising a protein hydrolysate of the invention additionally includes free arginine in an amount of from 0.1 to 2% by weight of protein and/or free histidine in an amount of from 0.1 to 3% by weight of protein. Addition of free arginine and/or free histidine is particularly preferred if modified sweet whey or whey protein isolate is used as the milk-based proteinaceous material in the process of the invention.

In another preferred embodiment, an infant formula composition comprising a protein hydrolysate of the invention is in the form of a nutritionally complete composition comprising an amount of milk-based protein hydrolysate of at least 5% dry solid, preferably about 10 to 30% dry solid.

EXAMPLES

Example 1

Microbial Alternative to Extracted Porcine Pancreatic Trypsin Preparation

Pancreatic Trypsin Novo 6.0S (available from Novozymes A/S—in the following PTN) is a product produced by extraction of porcine pancreatic tissue. The main components in PTN are trypsin and chymotrypsin with a ratio trypsin:chymotrypsin of at least 12.5:1 (activity basis, i.e. USP Trypsin Units:USP Chymotrypsin Units).

To identify a suitable microbial alternative to an extracted enzyme preparation like PTN, the activity at pH 9 of different microbial proteases on 10 different Suc-AAPX-pNA substrates available from Bachem (X=A, R, D, E, I, L, K, M, F and V) was measured. Based on these measurements, the Trypsin ratio (TR) and the Chymotrypsin ratio (CR) for each microbial protease were calculated. The Trypsin ratio and the Chymotrypsin ratio are defined as follows:

TR=max activity on Suc-AAP(R/K)-pNA/max activity on Suc-AAPnon(R/K)-pNA

CR=max activity on Suc-AAP(F/L/M)-pNA/max activity on Suc-AAPnon(F/L/M)-pNA

Trypsin Ratio:

Trypsins are specific serine endopeptidases that cleave on the carboxy terminal side of either an arginine residue or a lysine residue, i.e. they have a strict preference for R or K in the P1 position. Therefore, a reasonable definition of a trypsin-like protease is that the Trypsin ratio is >100, meaning that the activity on any of the 8 other Suc-AAPnon(R/K)-pNA substrates are less than 1% of the activity on the best Suc-AAP(R/K)-pNA substrate.

Chymotrypsin Ratio:

Chymotrypsins are known to have a less strict preference for cleaving on the carboxy terminal side of either aromatic amino acid residues (Trp, Tyr or Phe) or the hydrophobic amino acid residues Leu, Met and His. As compared to trypsin, chymotrypsin is a less specific endopeptidase, a reasonable definition of a chymotrypsin-like protease is that the Chymotrypsin ratio is >5, meaning that the activity on any of the 7 other Suc-AAPnon(F/L/M)-pNA substrates are less than 20% of the activity on the best Suc-AAP(F/L/M)-pNA substrate.

Suc-AAPX-pNA Assay:

Proteases: PTN

Porcine trypsin (UNIPROT:P00761)
  *Fusarium* trypsin (trypsin-like protease from *Fusarium oxysporum*, SEQ ID NO: 2)
  Bovine TLCK-treated chymotrypsin (Sigma, C-3142)
  Alcalase (available from Novozymes A/S)
  Bacillopeptidase F (from *B. licheniformis*, UNIPROT: Q65JX1)
  *Brachysporiella* protease (from *Brachysporiella gayana*, SEQ ID NO: 12)
  Esperase (available from Novozymes A/S)
  *Metarhizium* protease (from *Metarhizium anisopliae*, SEQ ID NO: 10)
  *Nocardiopsis* Protease (from *Nocardiopsis* sp. NRRL 18262, SEQ ID NO: 8)
  Savinase (available from Novozymes A/S)

Substrates: Suc-AAPA-pNA (Bachem L-1775)
  Suc-AAPR-pNA (Bachem L-1720)
  Suc-AAPD-pNA (Bachem L-1835)
  Suc-AAPE-pNA (Bachem L-1710)
  Suc-AAPI-pNA (Bachem L-1790)
  Suc-AAPL-pNA (Bachem L-1390)
  Suc-AAPK-pNA (Bachem L-1725)
  Suc-AAPM-pNA (Bachem L-1395)
  Suc-AAPF-pNA (Bachem L-1400)
  Suc-AAPV-pNA (Bachem L-1770)

Temperature: Room temperature (25° C.)

Assay buffer: 100 mM succinic acid, 100 mM HEPES, 100 mM CHES, 100 mM CABS, 1 mM $CaCl_2$, 150 mM KCl, 0.01% Triton X-100, pH 9.0.

Assay: 20 µl peptidase dilution (diluted in 0.01% Triton X-100) was placed in a well in a Microtiter plate. The assay was started by adding 200 µl pNA substrate (50 mg dissolved in 1.0 ml DMSO and further diluted 90× with the Assay buffer). The initial increase in OD405 was monitored as a measure of the peptidase activity. If a linear (or near linear) plot was not achieved in the 4 minutes measuring time, the peptidase was diluted further and the assay was repeated.

Data:

| Suc-AAPX-pNA | Porcine Trypsin | *Fusarium* Trypsin | Bovine Chymotrypsin | Alcalase | Bacillopeptidase F |
|---|---|---|---|---|---|
| Suc-AAPA-pNA | 0.0000 | 0.0000 | 0.0009 | 0.0250 | 1.0000 |
| Suc-AAPR-pNA | 1.0000 | 1.0000 | 0.0062 | 0.0118 | 0.5819 |
| Suc-AAPD-pNA | 0.0000 | 0.0000 | 0.0001 | 0.0005 | 0.7323 |
| Suc-AAPI-pNA | 0.0000 | 0.0000 | 0.0007 | 0.0003 | 0.0023 |
| Suc-AAPM-pNA | 0.0003 | 0.0000 | 0.3476 | 0.3758 | 0.6546 |
| Suc-AAPV-pNA | 0.0000 | 0.0000 | 0.0004 | 0.0003 | 0.3544 |
| Suc-AAPL-pNA | 0.0000 | 0.0000 | 0.2244 | 0.8650 | 0.0557 |
| Suc-AAPE-pNA | 0.0000 | 0.0000 | 0.0003 | 0.0029 | 0.0144 |
| Suc-AAPK-pNA | 0.5140 | 0.5307 | 0.0003 | 0.0190 | 0.1562 |
| Suc-AAPF-pNA | 0.0006 | 0.0000 | 1.0000 | 1.0000 | 0.0089 |
| Max of Suc-AAP(R/K)-pNA | 1.0000 | 1.0000 | 0.0062 | 0.0190 | 0.5819 |
| Max of Suc-AAPnon(R/K)-pNA | 0.0006 | 0.0000 | 1.0000 | 1.0000 | 1.0000 |
| Trypsin ratio | 1750 | >10000 | 0.006 | 0.019 | 0.58 |
| Max of Suc-AAP(F/L/M)-pNA | 0.0006 | 0.0000 | 1.0000 | 1.0000 | 0.6546 |
| Max of Suc-AAPnon(F/L/M)-pNA | 1.0000 | 1.0000 | 0.0062 | 0.0250 | 1.0000 |
| Chymotrypsin ratio | 0.0006 | 0.0000 | 160 | 40 | 0.65 |

| Suc-AAPX-pNA | Brachysporiella Protease | Esperase | Metarhizium Protease | Nocardiopsis Protease | Savinase |
|---|---|---|---|---|---|
| Suc-AAPA-pNA | 0.0185 | 0.1608 | 0.0237 | 0.1297 | 0.1031 |
| Suc-AAPR-pNA | 0.0456 | 0.0086 | 0.0374 | 0.0906 | 0.0013 |
| Suc-AAPD-pNA | 0.0084 | 0.0139 | 0.0075 | 0.0007 | 0.0004 |
| Suc-AAPI-pNA | 0.0009 | 0.0019 | 0.0007 | 0.0003 | 0.0001 |
| Suc-AAPM-pNA | 0.4439 | 1.0000 | 0.4210 | 0.7808 | 0.9177 |
| Suc-AAPV-pNA | 0.0027 | 0.0009 | 0.0020 | 0.0137 | 0.0006 |
| Suc-AAPL-pNA | 0.2838 | 0.6591 | 0.1940 | 0.1800 | 0.1789 |
| Suc-AAPE-pNA | 0.0007 | 0.0060 | 0.0004 | 0.0000 | 0.0082 |
| Suc-AAPK-pNA | 0.0219 | 0.0052 | 0.0264 | 0.0754 | 0.0097 |
| Suc-AAPF-pNA | 1.0000 | 0.3889 | 1.0000 | 1.0000 | 1.0000 |
| Max of Suc-AAP(R/K)-pNA | 0.0456 | 0.0086 | 0.0374 | 0.0906 | 0.0097 |
| Max of Suc-AAPnon(R/K)-pNA | 1.0000 | 1.0000 | 1.0000 | 1.0000 | 1.0000 |
| Trypsin ratio | 0.046 | 0.009 | 0.037 | 0.091 | 0.010 |
| Max of Suc-AAP(F/L/M)-pNA | 1.0000 | 1.0000 | 1.0000 | 1.0000 | 1.0000 |
| Max of Suc-AAPnon(F/L/M)-pNA | 0.0456 | 0.1608 | 0.0374 | 0.1297 | 0.1031 |
| Chymotrypsin ratio | 22 | 6.2 | 27 | 7.7 | 9.7 |

The reported activity data for each endopeptidase in the Table is relative to the activity for the best Suc-AAPX-pNA substrate.

Conclusion:

Using the above definition of a trypsin-like protease as a protease having a Trypsin ratio of >100, Porcine trypsin (TR=1750) and *Fusarium* trypsin (TR>10,000) are trypsin-like proteases. The rest of the tested proteases are not trypsin-like proteases.

Using the above definition of a chymotrypsin-like protease as a protease having a Chymotrypsin ratio of >5, Bovine chymotrypsin (CR=160), Alcalase (CR=40), *Brachysporiella* protease (CR=22), Esperase (CR=6.2), *Metarhizium* protease (CR=27), *Nocardiopsis* protease (CR=7.7) and Savinase (CR=9.7) are chymotrypsin-like proteases. The rest of the tested proteases are not chymotrypsin-like proteases.

An alternative definition of a chymotrypsin-like protease would be to calculate the sum of the squares of the relative activity differences to chymotrypsin. Using this definition, the *Metarhizium* protease comes out as the most chymotrypsin-like serine protease, followed by *Brachysporiella* protease, *Nocardiopsis* protease, Savinase and Alcalase (data not shown).

Example 2

Hydrolysis of WPC with Combinations of Microbial Endopeptidases

The next step was to see if it is possible to get the same degree of hydrolysis (DH) of a Whey Protein Concentrate (WPC) using a mixture of microbial endopeptidases as what can be obtained for PTN when the two enzyme mixtures are dosed equally.

Hydrolysis Experiments:

The hydrolysis assay we have performed was a two step hydrolysis procedure. 8.4% WPC (containing 80% whey protein) was suspended in pH 8.0 buffer. The first hydrolysis step was performed by adding half of the enzyme dose and incubating the solution with agitation for 2 hours at 55° C. Then the partly hydrolysed whey protein substrate was denatured by a short heating treatment (5 minutes at 90° C.). The second hydrolysis step was performed by adding the other half of the enzyme dose and incubating the solution with agitation for 30 minutes at 55° C. Finally, the enzyme reaction was stopped and the enzymes inactivated by another short heating treatment (10 minutes at 90° C.). The final concentration of whey protein/peptides was 6.4% WP. By using this assay we should be able to compare PTN with a microbial alternative.

As H+ is produced during hydrolysis in the alkaline range, we checked pH for some of the highest enzyme dosages. We couldn't detect any drop in pH, indicating that our pH 8.0 buffer is strong enough to control pH during hydrolysis.

First we tested 4 different doses of PTN (0.625, 1.25, 2.5 and 5.0 mg trypsin/g whey protein). For the lowest dose the whey protein hydrolysate was very viscous and almost impossible to get out of the Eppendorf tube and therefore DH wasn't determined for this hydrolysate. An SDS-PAGE analysis of the PTN hydrolysates showed that at least for the 5.0 mg trypsin/g whey protein dose, most of the intact proteins were degraded. On the following SDS-PAGE gel, equal amounts of protein/peptides are loaded on each lane. DH=9.4% for the 5.0 mg trypsin/g whey protein PTN dosage.

We then ran some hydrolysis experiments with purified trypsins (Porcine trypsin and *Fusarium* trypsin). We couldn't get a DH above approx. 6.5%, even at relatively high dosages. See the Data section below.

Finally, we ran a third series of hydrolysis experiments where we kept the dosage of the *Fusarium* trypsin constant at 5.0 mg trypsin/g whey protein and varied the chymotrypsin-like protease dosages (0.25, 0.5 and 1.0 mg protease/g whey protein). Here we obtained DH-values in the same range as PTN dosed equally (DH=9.4%).

It is seen that the effect on DH of increasing dosages of the second chymotrypsin-like protease have different effects depending on the second protease. The combination of *Fusarium* trypsin and Glutamyl peptidase BL from *Bacillus licheniformis* (which is not a chymotrypsin-like protease) seems to level off as was seen for *Fusarium* trypsin alone.

There is a correlation between the DH-values (see Data section below) and the appearance of the whey protein hydrolysates on SDS-PAGE gels. A combination of *Fusarium* trypsin and *Nocardiopsis* protease seem (from the SDS-PAGE gels—not shown) to be the best serine protease combination to remove intact proteins from the WPC substrate.

Hydrolysis Assay:

Endopeptidases Used:

| Enzyme | Trypsin Conc. (mg/ml) | Chymotrypsin Conc. (mg/ml) |
| --- | --- | --- |
| PTN 6.0S | 187 mg/g (1310 USP/mg) | 18.7 mg/g (84 USP/mg) |
| Porcine trypsin | 3.1 | |
| *Fusarium* trypsin | 8.0 | |
| *Metarhizium* protease | | 2.6 |
| *Brachysporiella* protease | | 10.6 |
| Alcalase | | 19.6 |
| *Nocardiopsis* protease | | 8.8 |
| Glutamyl peptidase BL | 3.7 | |

For calculation of the trypsin and chymotrypsin content in PTN 6.0S, we have used a specific activity for Porcine trypsin=7000 USP/mg and a specific activity for Porcine chymotrypsin=4500 USP/mg. The enzyme concentration in the other preparations was estimated from A280/E280. PTN was dissolved in 20 mM HEPES/NaOH, 5 mM $CaCl_2$, pH 8. Other enzymes were used "as is" after thawing.

Hydrolysis:

84 mg/ml WPC (LactProdan80 from Arla comprising about 80% protein of total dry matter) was suspended in 1.0 M HEPES/NaOH, 50 mM $CaCl_2$, pH 8.0 and the pH was adjusted to pH 8.0 with 27% NaOH. 1000 µl of this suspension was placed in an Eppendorf tube on ice. 25 µl Peptidase solution was added and the Eppendorf tube was transferred to an Eppendorf thermomixer prewarmed to 55° C. The tube was incubated for 120 minutes on the thermomixer (55° C., 1400 rpm). The tube was then transferred to another Eppendorf thermomixer which was prewarmed to 90° C. and incubated for 5 minutes on this thermomixer (90° C., 1400 rpm). The tube was transferred back to the first 55° C. Eppendorf thermomixer and after 5 minutes (to bring the hydrolysis mixture back to 55° C.), 25 µl Peptidase solution was added and the tube was incubated for 30 minutes on the thermomixer (55° C., 1400 rpm). Finally, the tube was again transferred to the 90° C. thermomixer and incubated for 10 minutes on this thermomixer (90° C., 1400 rpm).

The hydrolysate (with 64 mg/ml whey protein) was analysed by SDS-PAGE (not shown) and DH was measured using the OPA method.

SDS-PAGE:

The hydrolysate was diluted 5× in 0.1% SDS. 20 µl of this dilution was mixed with 20 µl 2×SDS-PAGE sample buffer with reducing agent. This mixture was boiled and 10 µl was applied to a 4-20% Tris-glycine gel.

OPA Method for Measuring DH:

The hydrolysate was diluted 80× in 0.01% Triton X-100. 30 µl of this dilution was transferred to a MicroTiterPlate (MTP) and 225 µl freshly prepared OPA reagent was added and after 2 minutes the absorbance at 340 nm was read in a MTP reader. The response of unknown samples were compared with a serine standard dilution series and expressed as mg/ml serine. "OPA response" was calculated as "mg/ml serine in the hydrolysate" relative to "mg/ml substrate". The "OPA response" of the Enzyme blank was subtracted for calculation of DH.

OPA Reagent:

3.81 g Di-sodium tetraborate (Merck 6308) and 1.00 g SDS (BIO-RAD 161-0301) was dissolved in 80 ml deionised water. Just before use, 80 mg o-phtaldialdehyde (Merck 821027) dissolved in 2.0 ml ethanol was added and 1.0 ml 10% (w/v) DTE (Merck 24511). Finally, the volume was adjusted to 100 ml with deionised water.

Data:

| Enzyme | Dosage | | Total | |
| --- | --- | --- | --- | --- |
| | Trypsin (mg/g WP) | Chymotrypsin (mg/g WP) | "OPA response" (%) | DH (%) |
| Blank | 0 | 0 | 9.4 | 0.0 |
| PTN | 1.25 | 0.125 | 16.6 | 7.2 |
| PTN | 2.5 | 0.25 | 17.3 | 7.9 |
| PTN | 5 | 0.5 | 18.8 | 9.4 |
| Porcine trypsin | 2.5 | | 15.8 | 6.4 |
| Porcine trypsin | 5 | | 16.0 | 6.6 |
| *Fusarium* trypsin | 5 | | 15.5 | 6.1 |
| *Fusarium* trypsin | 10 | | 15.9 | 6.5 |
| Blank | 0 | 0 | 9.5 | 0.0 |
| *Fusarium* trypsin + *Metarhizium* | 5 | 0.25 | 18.1 | 8.6 |
| *Fusarium* trypsin + *Metarhizium* | 5 | 0.5 | 19.3 | 9.8 |
| *Fusarium* trypsin + *Metarhizium* | 5 | 1.0 | 21.6 | 12.1 |
| *Fusarium* trypsin + *Brachysporiella* | 5 | 0.25 | 17.3 | 7.8 |
| *Fusarium* trypsin + *Brachysporiella* | 5 | 0.5 | 17.9 | 8.4 |
| *Fusarium* + *Brachysporiella* | 5 | 1.0 | 19.1 | 9.6 |
| *Fusarium* trypsin + Alcalase | 5 | 0.25 | 19.6 | 10.1 |
| *Fusarium* trypsin + Alcalase | 5 | 0.5 | 22.4 | 12.9 |
| *Fusarium* trypsin + Alcalase | 5 | 1.0 | 24.1 | 14.6 |
| *Fusarium* trypsin + *Nocardiopsis* | 5 | 0.25 | 19.1 | 9.6 |
| *Fusarium* trypsin + *Nocardiopsis* | 5 | 0.5 | 20.0 | 10.5 |
| *Fusarium* trypsin + *Nocardiopsis* | 5 | 1.0 | 21.0 | 11.5 |
| *Fusarium* + Glutamyl peptidase BL | 5 | 0.25 | 18.9 | 9.4 |
| *Fusarium* + Glutamyl peptidase BL | 5 | 0.5 | 19.4 | 9.9 |
| *Fusarium* + Glutamyl peptidase BL | 5 | 1.0 | 19.8 | 10.3 |

Conclusion:

It seems to be possible to get the same degree of hydrolysis (DH) of WPC using a microbial PTN-replacer (dosed as PTN). It is also obvious from the results that a trypsin-like protease alone will not be able to give the same DH as PTN.

Example 3

Cleavage Specificity Analysis of *Fusarium* Trypsin and *Brachysporiella* Endopeptidase Introduction:

The proteolytic cleavage specificity of the microbial trypsin-like endopeptidase, *Fusarium* trypsin, was compared with porcine trypsin. And the proteolytic cleavage specificity of the microbial chymotrypsin-like endopeptidase from *Brachysporiella* was compared with the proteolytic specificity of TLCK treated porcine chymotrypsin. (TLCK inactivates trypsin activity without effecting chymotrypsin).

The cleavage specificity analyses were performed by incubation of the described endopeptidases with the denatured model substrate bovine beta-lactoglobulin A. The sequences of the resulting proteolytic peptides were determined by online RP-HPLC-ESI-Orbitrap MS/MS combined with a tandem mass spectrometry data analysis program used for protein identification (SEQUEST) and a database containing only bovine beta-lactoglobulin A.

Samples:

Proteases: Porcine trypsin (UniProt accession: P00761)
  *Fusarium* trypsin (trypsin-like protease from *Fusarium oxysporum*, SEQ ID NO: 2)
  Bovine TLCK treated chymotrypsin (Sigma, C-3142)
  *Brachysporiella* protease (from *Brachysporiella gayana*, SEQ ID NO. 12)

Substrate: Beta-lactoglobulin A, from bovine milk (Sigma L7880 097K7010, SEQ ID NO: 13)

Proteolysis:

Denaturation of Beta-Lactoglobulin A:

An amount of ca. 11 mg Beta-lactoglobulin A from bovine milk (Sigma L7880 097K7010) was dissolved in 1 ml buffer (100 mM ammoniumacetat, 1 mM $CaCl_2$ pH8. The disulfide bridges of beta-lactoglobulin were reduced by addition of dithiothreitol (DTT, CAS number 3483-12-3) to a final concentration of 20 mM. The mixture was incubated at room temperature (25° C.) for 30 min. Subsequently 2-Iodoacetamide (CAS number 144-48-9) was added to a final concentration of 55 mM. The latter mixture was incubated in darkness and at room temperature for 30 min.

The denatured beta-lactoglobulin A was buffer changed to 100 mM ammoniumacetat, 1 mM $CaCl_2$ pH8 prior to incubation with the proteases. Buffer change was performed on a PD-10 Desalting column from GE-healthcare (Sephadex G-25 column material). First the column was equilibrated with 25 ml 100 mM ammoniumacetat, 1 mM $CaCl_2$ pH8. The beta-lactoglobulin sample volume was adjusted to a final volume of 2.5 ml with equilibration buffer and loaded on the column. Beta-lactoglobulin A was eluted with 3.5 ml 100 mM ammoniumacetat, 1 mM $CaCl_2$ pH8. The final protein concentration of the buffer changed beta-lactoglobulin was determined to 2 mg/ml by spectrophotometric analysis at 280 nm and an estimated extinction (A280) coefficient of 1.

Proteolytic Incubation:

An amount of 400 µg beta-lactoglobulin corresponding to 190 µl solution was incubated at 40° C. with the following amount of proteases:

| Porcine trypsin | 8 µg |
| --- | --- |
| *Fusarium* trypsin | 16 µg |
| Bovine TLCK treated chymotrypsin | 4 µg |
| *Brachysporiella* protease | 4 µg |

The proteolysis process was stopped after 18 hours by addition of aqueous solution of 10% trifluoroacetic acid (TFA, CAS number 76-05-1) to a final concentration of 1% TFA in the sample. All samples were stored at −20° C. prior analysis by LC-MS/MS LC-MS/MS Method:

All proteolytic samples were analyzed on a RP-HPLC-ESI-Orbitrap MS/MS system consisting of Waters C18 column (ACQUITY HPLC® BEH C18, 1.7 μm, 2.1×100 mm), an Accela liquid chromatography system from Thermo Scientific and a LTQ Orbitrap XL ETD hybrid mass spectrometer from Thermo Scientific. A volume of 20 μl was injected onto the column. The peptides were separated by the following gradient:

Solvent A: 0.1% formic acid (CAS number 64-18-6) in UHQ water and solvent B: 0.1% formic acid in acetonitrile (CAS number 75-05-8)

| Time (min) | % B solvent |
| --- | --- |
| 0 | 5 |
| 2 | 5 |
| 49 | 50 |
| 51 | 90 |
| 53 | 90 |
| 55 | 5 |
| 60 | 5 |

Figure 2:
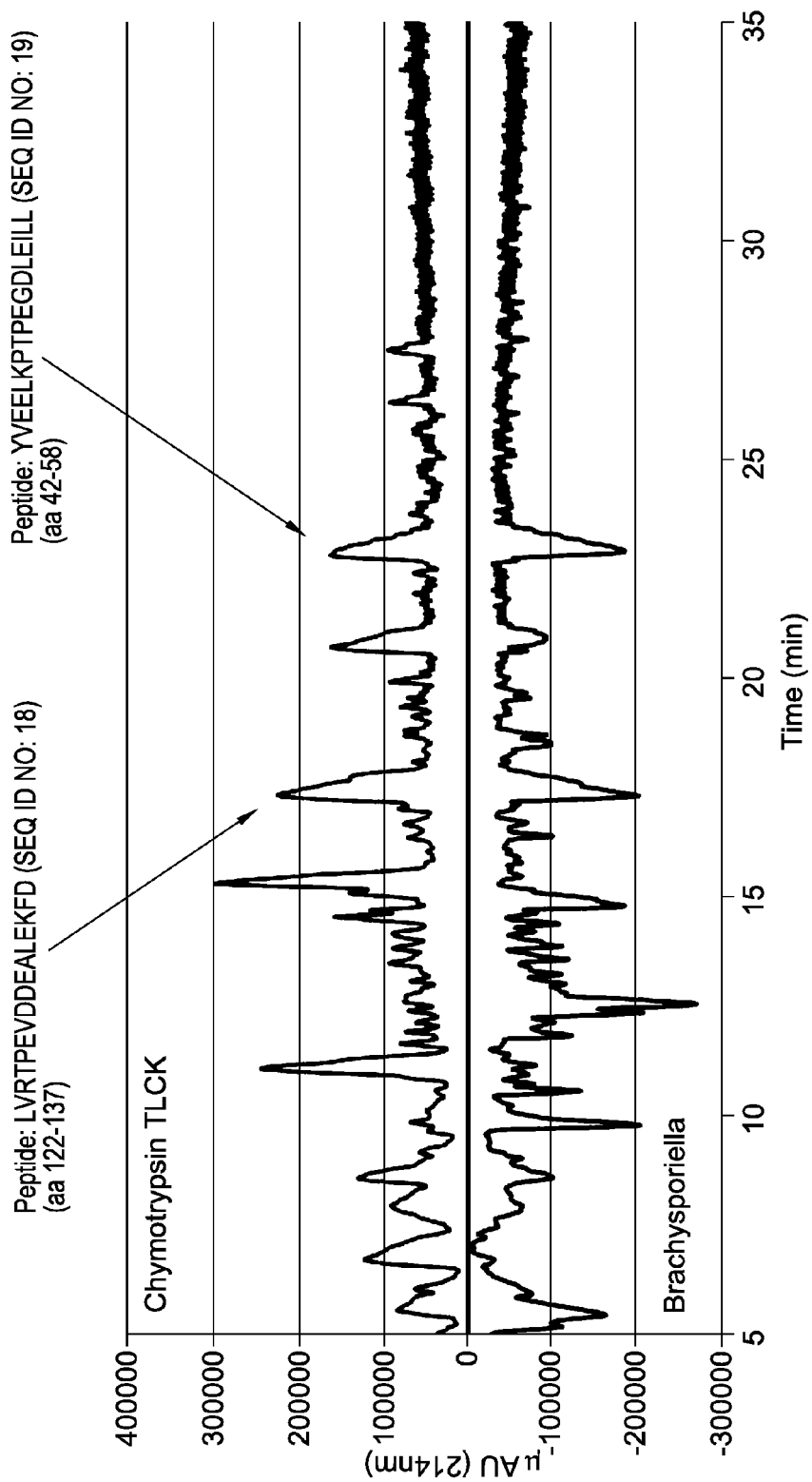
FIG. 2 shows UV-chromatograms of *Brachysporiella* protease (bottom trace) compared with bovine chymotrypsin (upper trace) and the peptide sequence identity of some major peaks are displayed.

The eluting peptides were monitored online by a UV-detector at 214 nm and subsequently online by a mass spectrometer in MS/MS mode. The resulting UV-chromatograms are shown in FIGS. 1 and 2. The precursor ion in the mass spectrometer was detected at a resolution of 30,000 (FWHM) and the fragment ions at a resolution of 15,000 (FWHM). The resulting MS and MS/MS spectra were analyzed with SEQUEST software (algorithm subject to U.S. Pat. Nos. 6,017,693 and 5,538,897) via Proteome Discoverer (version 1.0, Thermo Fisher Scientific) against beta-lactoglobulin. The cleaving enzyme was defined as "No-enzyme" with "unspecific" cleavage specificity. Proteolytic fragments of some of the high intensive UV-peaks were identified as indicated in the FIGS. 1 and 2.

Results:

For comparison the UV-chromatogram of the *Fusarium* trypsin assay (bottom trace) is displayed in FIG. 1 together with porcine trypsin assay (upper trace) and the sequence identity of some major peptides are displayed. Likewise, in FIG. 2, the UV-chromatogram of *Brachysporiella* protease assay (bottom trace) is displayed together with bovine chymotrypsin (upper trace). In all cases, the identified peptides have been detected in both the upper and the bottom trace.

Conclusion:

In FIG. 1, common proteolytic peptides of bovine beta-lactoglobulin A are detected for *Fusarium* trypsin and porcine trypsin, thus the two endoproteases both have trypsin like specificity. In FIG. 2, some common proteolytic peptides of bovine beta-lactoglobulin A are detected for *Brachysporiella* protease and bovine chymotrypsin.

The invention claimed is:

1. A process for the preparation of a milk-based protein hydrolysate comprising treatment of a solution of a milk-based proteinaceous material with
   a) a trypsin-like endopeptidase produced from a microorganism and comprising an amino acid sequence having at least 95% identity to the mature polypeptide of SEQ ID NO: 2, wherein the trypsin-like endopeptidase is from a strain of *Fusarium*, and
   b) at least one other endopeptidase produced from a microorganism and comprising an amino acid sequence having at least 95% identity to the mature polypeptide of SEQ ID NO: 8, wherein the at least one other endopeptidase is from a strain of *Nocardiopsis*.

2. The process of claim 1, wherein the ratio of trypsin-like endopeptidase to milk-based protein is 0.01-10% weight/weight.

3. The process of claim 1, wherein the ratio of the at least one other endopeptidase to milk-based protein is 0.001-1% weight/weight.

4. The process of claim 1, comprising adding the at least one other endopeptidase at a concentration which is between 2% and 50% of the concentration of trypsin-like endopeptidase based on the weight of the endopeptidases.

5. The process of claim 1, comprising conducting hydrolysis at a temperature of about 40° C. to 60° C., during 1 to 6 hours, at pH values within the range 6.5 to 8.5.

6. The process of claim 1, further comprising adding the milk-based protein hydrolysate obtained into an infant formula composition.

7. The process of claim 1, wherein the trypsin-like endopeptidase is a polypeptide comprising an amino acid sequence having at least 98% identity to the mature polypeptide of SEQ ID NO: 2.

8. The process of claim 1, wherein the trypsin-like endopeptidase is a polypeptide comprising an amino acid sequence having at least 98% identity to the mature polypeptide of SEQ ID NO: 8.

* * * * *